(12) United States Patent
Sakamoto

(10) Patent No.: US 10,354,360 B2
(45) Date of Patent: Jul. 16, 2019

(54) MEDICAL IMAGE DISPLAY APPARATUS, DISPLAY CONTROL METHOD THEREFOR, AND NON-TRANSITORY RECORDING MEDIUM

(71) Applicant: CANON KABUSHIKI KAISHA, Tokyo (JP)

(72) Inventor: Tsuyoshi Sakamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 33 days.

(21) Appl. No.: 15/085,825

(22) Filed: Mar. 30, 2016

(65) Prior Publication Data
US 2016/0292818 A1 Oct. 6, 2016

(30) Foreign Application Priority Data

Mar. 31, 2015 (JP) .................................. 2015-074604

(51) Int. Cl.
*G09G 5/00* (2006.01)
*G06T 3/40* (2006.01)
(Continued)

(52) U.S. Cl.
CPC ............... *G06T 3/40* (2013.01); *A61B 6/463* (2013.01); *A61B 6/466* (2013.01); *A61B 6/504* (2013.01);
(Continued)

(58) Field of Classification Search
CPC ............................. G09G 5/391; G06T 3/4007
(Continued)

(56) References Cited

U.S. PATENT DOCUMENTS

2004/0249270 A1 12/2004 Kondo
2005/0110791 A1* 5/2005 Krishnamoorthy ....... G06T 7/60
345/419
(Continued)

FOREIGN PATENT DOCUMENTS

CN 1864635 A 11/2006
CN 102592307 A 7/2012
(Continued)

OTHER PUBLICATIONS

L. Zhu, S. Haker, and A. Tannenbaum. Flattening maps for the visualization of multibranched vessels. IEEE Transactions on Medical Imaging, 24(2):191-198, 2005.*
(Continued)

*Primary Examiner* — Jin Ge
(74) *Attorney, Agent, or Firm* — Canon USA Inc., IP Division

(57) ABSTRACT

A medical image display apparatus includes a display unit that displays at least partial paths of a plurality of paths of a tubular structure identified from a medical image, the at least partial paths including a first path and a second path that are displayed separately from each other, and a display magnification determining unit that determines at least one of a display magnification and a display position of at least one of the displayed first and second path based on whether the first path and the second path has a common part to each other, wherein the display unit displays the first path and the second path and displays one of the first path and the second path at a determined display magnification.

38 Claims, 23 Drawing Sheets

(51) Int. Cl.
| | |
|---|---|
| *G09G 5/373* | (2006.01) |
| *G09G 5/38* | (2006.01) |
| *A61B 6/00* | (2006.01) |
| *G06T 19/00* | (2011.01) |
| *A61B 6/03* | (2006.01) |
| *G09G 3/00* | (2006.01) |

(52) U.S. Cl.
CPC .......... *A61B 6/5217* (2013.01); *A61B 6/5223* (2013.01); *G06T 19/00* (2013.01); *G09G 5/373* (2013.01); *G09G 5/38* (2013.01); *A61B 6/032* (2013.01); *G06T 2210/41* (2013.01); *G06T 2219/028* (2013.01); *G09G 3/003* (2013.01); *G09G 2340/02* (2013.01); *G09G 2340/045* (2013.01); *G09G 2380/08* (2013.01)

(58) Field of Classification Search
USPC .......................................................... 345/667
See application file for complete search history.

(56) References Cited

U.S. PATENT DOCUMENTS

| | | | | |
|---|---|---|---|---|
| 2006/0056685 | A1* | 3/2006 | Kiraly | G06T 7/0012 382/165 |
| 2006/0262970 | A1* | 11/2006 | Boese | G03B 42/023 382/131 |
| 2007/0035564 | A1* | 2/2007 | Katsuyama | H04N 1/00408 345/649 |
| 2009/0080744 | A1* | 3/2009 | Sagawa | G06F 19/321 382/131 |
| 2009/0086912 | A1* | 4/2009 | Sakaguchi | A61B 5/02007 378/98.5 |
| 2009/0169076 | A1* | 7/2009 | Lobregt | A61B 5/055 382/128 |
| 2009/0278846 | A1* | 11/2009 | Gulsun | G06T 7/60 345/423 |
| 2010/0053160 | A1* | 3/2010 | Arakita | G06T 15/08 345/424 |
| 2010/0220917 | A1* | 9/2010 | Steinberg | G06T 7/0022 382/134 |
| 2010/0289825 | A1* | 11/2010 | Shin | G06F 3/04845 345/667 |
| 2011/0105879 | A1* | 5/2011 | Masumoto | G06F 19/321 600/407 |
| 2012/0083696 | A1* | 4/2012 | Kitamura | G06T 7/0028 600/443 |
| 2012/0093388 | A1* | 4/2012 | Masumoto | G06T 7/0012 382/134 |
| 2012/0188240 | A1* | 7/2012 | Hirano | G06T 15/08 345/419 |
| 2013/0009958 | A1* | 1/2013 | Kitamura | A61B 6/032 345/424 |
| 2013/0106910 | A1* | 5/2013 | Sacco | G06T 19/006 345/633 |
| 2014/0355858 | A1* | 12/2014 | O'Dell | G06T 7/0081 382/131 |
| 2015/0010225 | A1* | 1/2015 | Popovic | A61B 1/00009 382/131 |
| 2017/0318235 | A1* | 11/2017 | Schneider | H04N 5/2628 |

FOREIGN PATENT DOCUMENTS

| | | |
|---|---|---|
| JP | 2004283373 A | 10/2004 |
| JP | 2011206155 A | 10/2011 |
| JP | 2012245170 A | 12/2012 |

OTHER PUBLICATIONS

Pal'agyi, K., Tschirren, J., Hoffman, E.A., Sonka, M., 2006. Quantitative analysis of pulmonary airway tree structures. Comput. Biol. Med. 36 (9), 974-996.*

* cited by examiner

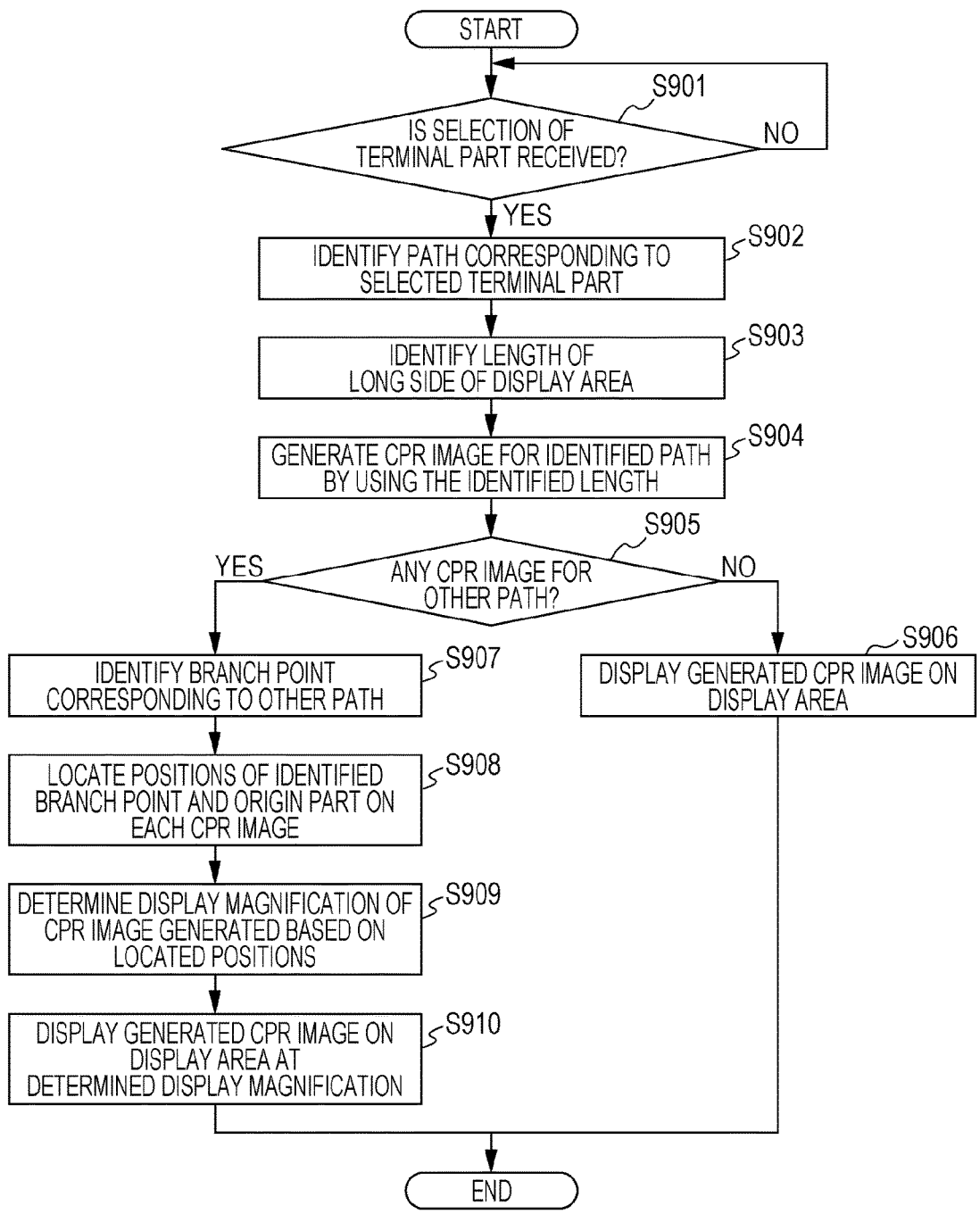

MEDICAL IMAGE DISPLAY APPARATUS, DISPLAY CONTROL METHOD THEREFOR, AND NON-TRANSITORY RECORDING MEDIUM

BACKGROUND

Field

Aspects of the present invention generally relate to a medical image diagnosis apparatus that displays at a proper display magnification a path including a branch point identical to that of another path in a tubular structure when the paths are displayed, a control method therefor, and a program.

Description of the Related Art

A medical-image display mechanism exists which displays a tubular structure such as a blood vessel and the intestines as a three-dimensional medical image acquired by performing volume rendering by superimposing two-dimensional medical images of X-ray CT or MRI, for example.

Curved Multi Planer Reconstruction (hereinafter, CPR) is a technology for reconstructing multiple planes of a three-dimensional medical image. U.S. Patent Application Publication No. 2004/0249270 discloses a technology which generates a straightened CPR image acquired by drawing a curved line along a centerline of a tubular structure in a longitudinal direction thereof and converting the curved line to a straight line.

A CPR image may show the entire length of a tubular structure running three-dimensionally and the diameter of a blood vessel within which a treatment is performed using a stent graft on one screen and may therefore be used for examining a place to insert a catheter.

However, the technology disclosed in US 2004/0249270 and conventional technologies have a problem that the size of a CPR image depends on the display area of the CPR image.

For example, FIG. 24 illustrates a screen having a display area 2401a displaying a CPR image showing a path from an origin part to a terminal part D7 of a tubular structure illustrated in FIG. 6 and a display area 2401b displaying a CPR image showing a path from the origin part to a terminal part D3 of the tubular structure. These two paths are identical up to a branch point B3 as illustrated in FIG. 6. However, for clearly showing the shorter path, the CPR image is generated by using the length of the longer side of the display area 2401. As a result, the paths are difficult to be compared though they are identical.

SUMMARY OF THE INVENTION

Aspects of the present invention generally provide a mechanism enabling displays of paths including branch points of a tubular structure wherein a first path including a branch point identical to that of a second path is displayed at a proper display magnification.

According to an aspect of the present invention, there is provided a medical image display apparatus including a display unit configured to display at least partial paths of a plurality of paths of a tubular structure identified from a medical image, the at least partial paths including a first path and a second path that are displayed separately from each other, and a display magnification determining unit configured to determine at least one of a display magnification and a display position of at least one of the first path and the second path displayed in the display unit based on whether the first path and the second path has a common part to each other, wherein the display unit displays the first path and the second path and displays one of the first path and the second path at a display magnification determined by the display magnification determining unit.

Further features of aspects of the present invention will become apparent from the following description of exemplary embodiments with reference to the attached drawings.

BRIEF DESCRIPTION OF THE DRAWINGS

FIG. 9 is a flowchart illustrating an example of a flow of processing for displaying a CPR image from an origin part to a selected terminal part of a tubular structure.

DESCRIPTION OF THE EMBODIMENTS

Embodiments of the present invention will be described in detail below with reference to drawings. A first embodiment will be described first.

Figure 1:
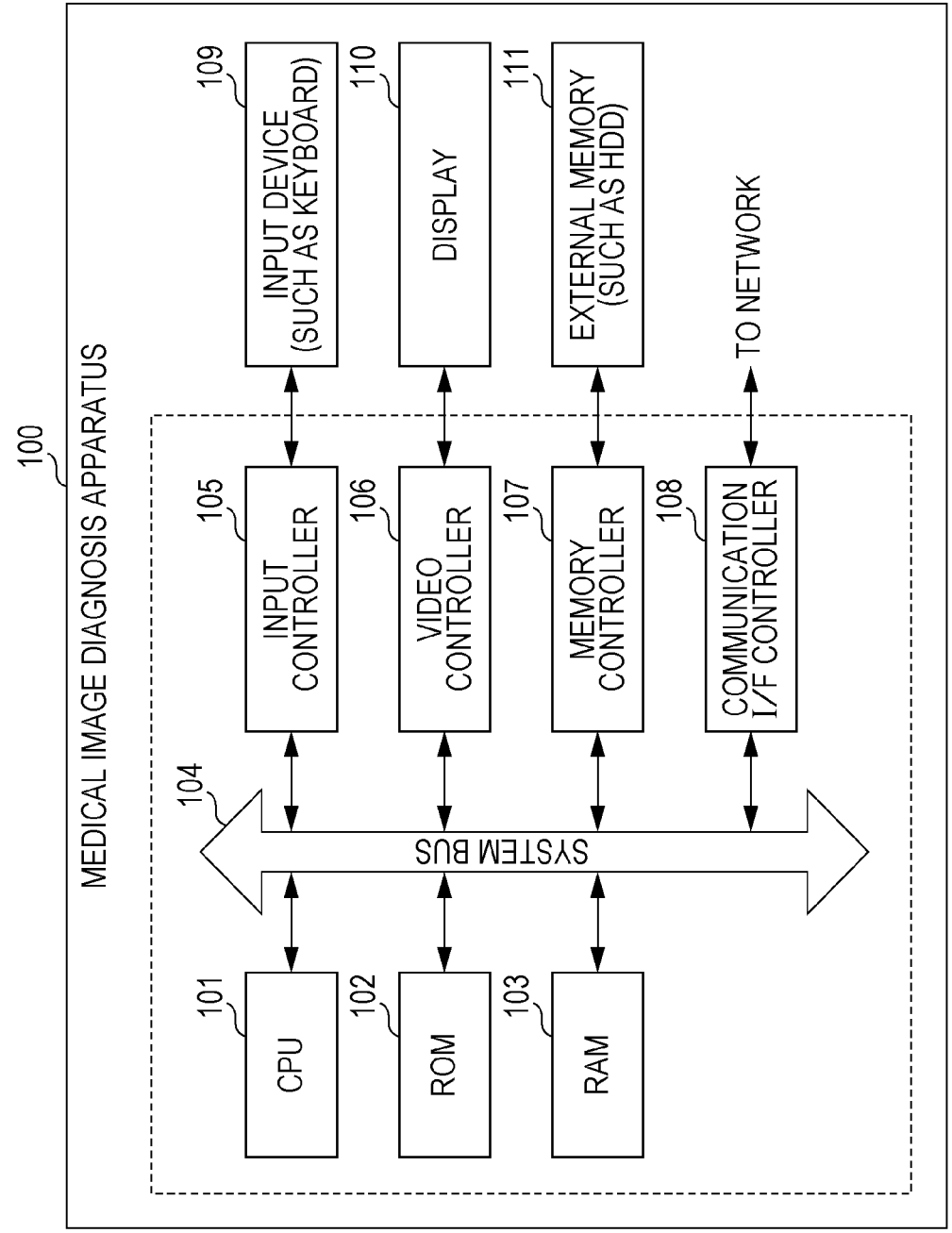
FIG. 1 illustrates an example of a hardware configuration of a medical image diagnosis apparatus.

FIG. 1 illustrates an example of a hardware configuration of a medical image diagnosis apparatus 100. It should be understood that the hardware configuration of the medical image diagnosis apparatus 100 is not limited to the one illustrated in FIG. 1.

The medical image diagnosis apparatus 100 is configured to generate a three-dimensional medical image from CT or MRI two-dimensional medical images and generate a CPR image by identifying a tubular structure from the three-dimensional medical image. The medical image diagnosis apparatus 100 may be a so-called personal computer or may be a server apparatus. The medical image diagnosis apparatus 100 may be a tablet terminal or a mobile terminal having a touch panel.

A CPU 101 generally controls devices and controllers connected to a system bus 104.

A ROM 102 or an external memory 111 stores a BIOS (Basic Input/Output System) and an operating system program, which are control programs for the CPU 101. The external memory 111 stores programs necessary for implementing functions. A RAM 103 functions as a main memory and a work area for the CPU 101.

The CPU 101 loads to the RAM 103 a program necessary for execution of a process and executes the program to implement its corresponding operation.

An input controller 105 controls an input from an input device 109 such as a keyboard and a pointing device such as a mouse.

A video controller 106 controls display on a display device such as a display 110. The type of display device assumed here is a CRT or a liquid crystal display, but it is not limited thereto.

A memory controller 107 controls access to the external memory 111 such as a hard disk, a flexible disk, or a card type memory connected to a PCMCIA card slot through an adapter. The external memory 111 (storage unit) may store data of a boot program, browser software, an application, font data, a user file, an edited file, and so on.

A communication I/F controller 108 is communicably coupled to an external apparatus over a network and executes a communication control process over the network. For example, the communication I/F controller 108 may be used for the Internet communication based on TCP/IP.

It should be noted that the CPU 101 performs rasterizing processing on an outline font for a display information region within the RAM 103, for example, so that it can be displayed on the display 110. The CPU 101 enables a user to instruct with a mouse cursor, not illustrated, on the display 110.

A program that is used for execution of a process, which will be described below, by the medical image diagnosis apparatus 100 is stored in the external memory 111 and is loaded to the RAM 103 as required so that it can be executed by the CPU 101. A definition file and information tables usable by a program according to aspects of the present invention are also stored in the external memory 111.

Figure 2:
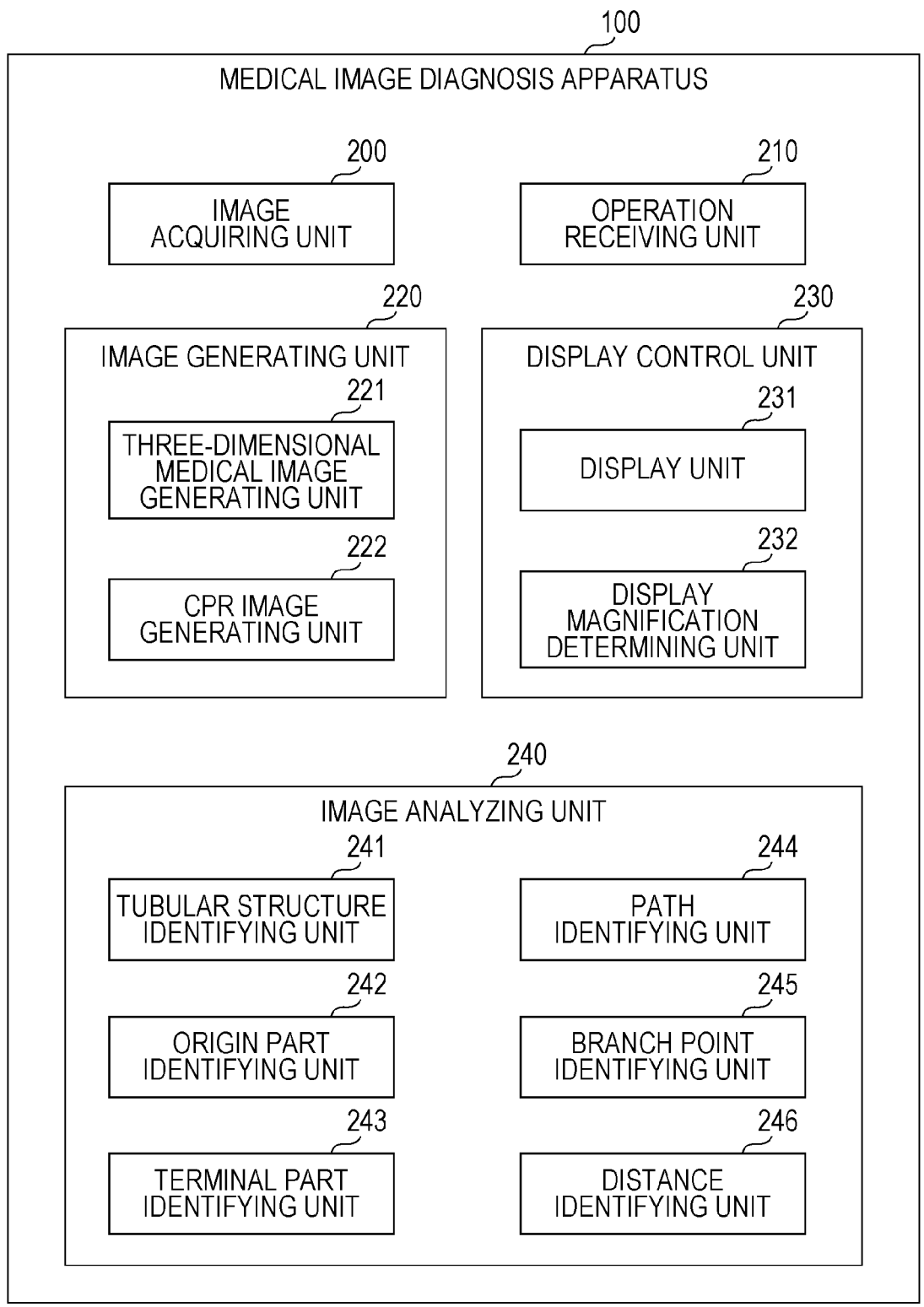
FIG. 2 illustrates an example of a functional configuration of the medical image diagnosis apparatus.

FIG. 2 illustrates an example of a functional configuration of the medical image diagnosis apparatus 100. It should be noted that functions illustrated in FIG. 2 are components implemented by hardware and programs illustrated in FIG. 1. The functional configuration of the medical image diagnosis apparatus 100 is not limited thereto.

The medical image diagnosis apparatus 100 includes functional components of an image acquiring unit 200, an operation receiving unit 210, an image generating unit 220, a display control unit 230, and an image analyzing unit 240.

The image acquiring unit 200 is a functional unit configured to acquire a two-dimensional medical image acquired by a modality apparatus such as an X-ray CT apparatus and an MRI apparatus. A plurality of CT images of a subject acquired by a multi-slice X-ray CT apparatus, for example, corresponding to the image acquiring unit 200 will be described below.

The operation receiving unit 210 (selection receiving unit) is a functional unit configured to receive an operation from a user input on a screen displayed on the display 110. The input device 109 is operated by a user to receive a selection or an instruction regarding a tubular structure displayed on a screen or a selection input on a selection form such as a check box or a radio button.

The image generating unit 220 is a functional unit configured to generate a three-dimensional medical image and a CPR image showing a three-dimensional model of a subject. The image generating unit 220 includes a three-dimensional medical image generating unit 221, and a CPR image generating unit 222.

The three-dimensional medical image generating unit 221 is a functional unit configured to generate a three-dimensional medical image based on a publicly known scheme such as volume rendering based on a plurality of two-dimensional medical images acquired by the image acquiring unit. The opacity or a CT value of volume data of a three-dimensional medical image may be changed in accordance with an instruction from a user so that only a specific structure can be extracted and be displayed.

The CPR image generating unit 222 (cross-sectional image generating unit) is a functional unit configured to generate a CPR image (cross-sectional image) showing at least a partial range of a tubular structure which is an objective within a three-dimensionally converted medical image. A CPR image may be a straightened CPR image or may be a stretched CPR image or a projected CPR image. The CPR image generating unit 222 may generate a CPR image of a whole tubular structure whether or not it is required to be displayed or may generate a CPR image only showing a range designated as an observation range. The observation range may be determined automatically or may be determined based on a designation input from a user.

The display control unit 230 is a functional unit configured to control display of information on the display 110. The display control unit 230 includes a display unit 231 and a display magnification determining unit 232.

The display unit 231 is a functional unit configured to display an image generated by the image generating unit 220 on the display 110. When the display magnification determining unit 232 designates a display magnification for an image, the size of the image is enlarged or reduced in accordance with the display magnification for display.

The display magnification determining unit 232 is a functional unit configured to determine a display magnification for a CPR image generated by the CPR image generating unit 222. When the display unit 231 displays a CPR image, the display magnification determining unit 232 identifies the position of an identical branch point on the CPR image and another CPR image and determines the display magnification in accordance with the position.

The image analyzing unit 240 is a functional unit configured to analyze a three-dimensional medical image and a CPR image generated by the image generating unit 220. The image analyzing unit 240 includes tubular-structure identifying unit 241, an origin part identifying unit 242, a terminal part identifying unit 243, a path identifying unit 244, a branch-point identifying unit 245, and a distance identifying unit 246.

The tubular-structure identifying unit 241 is a functional unit configured to identify an objective tubular structure from a three-dimensional medical image generated by the three-dimensional medical image generating unit 221. For example, in order to identify a tubular structure from an ascending aorta to right and left femoral arteries and deep femoral arteries, a central part of the aorta is detected based on a characteristic that a circular and central region of an object having a CT value or 100 or higher has a higher CT value than a range on an outer side. A shape having a similar characteristic from the detected region is traced in all directions, and the tracing completes at the end of the shape. Here, the region of the heart in which the tracing has completed is defined as an origin part of the aorta, and the other part is defined as terminal parts. Then, the tubular structure from the origin part to the terminal parts can be identified as a region from the ascending aorta to the right and left femoral arteries and deep femoral arteries. It should be understood that the method for identifying an objective tubular structure is not limited thereto. Any publicly known method may be used.

The origin part identifying unit 242 is a functional unit configured to identify the region of the heart in which the tracing has completed as a result of the tracing performed by the tubular-structure identifying unit 241. The terminal part identifying unit 243 is a functional unit configured to identify the parts excluding the region having undergone the tracing as terminal parts as a result of the tracing performed by the tubular-structure identifying unit 241.

The path identifying unit 244 is a functional unit configured to identify the core line (centerline) of the tubular structure identified by the tubular-structure identifying unit 241 as a path from the origin part identified by the origin part identifying unit 242 to the terminal part identified by the terminal part identifying unit 243. A core line of a tubular structure is a set of center points (or center-of-gravity points) of a vertical cross section about an axis direction of the tubular structure. The center points are identified from the origin part to a terminal part and are connected to identify a core line. The core line is identified as a path to the terminal part.

The branch-point identifying unit 245 is a functional unit configured to identify a part where the core line of the tubular structure identified by the tubular-structure identifying unit 241 diverges. A tubular structure of a blood vessel, for example, diverges into a plurality of paths because it is a tree structure. The branch-point identifying unit 245 identifies branch points from branch points of the core line.

The distance identifying unit 246 is a functional unit configured to identify the distance between two points on the path of the tubular structure identified by the path identifying unit 244. Because a three-dimensional medical image showing a tubular structure is generated from two-dimensional medical images, an actual value of a subject can be acquired from the two-dimensional medical images in accordance with DICOM (Digital Imaging and Communication in Medicine). Based on the value, the distance between two points on the path of the tubular structure is identified.

Next, a flow of processing for analyzing a tubular structure will be described with reference to FIGS. 3 to 8.

Figure 3:
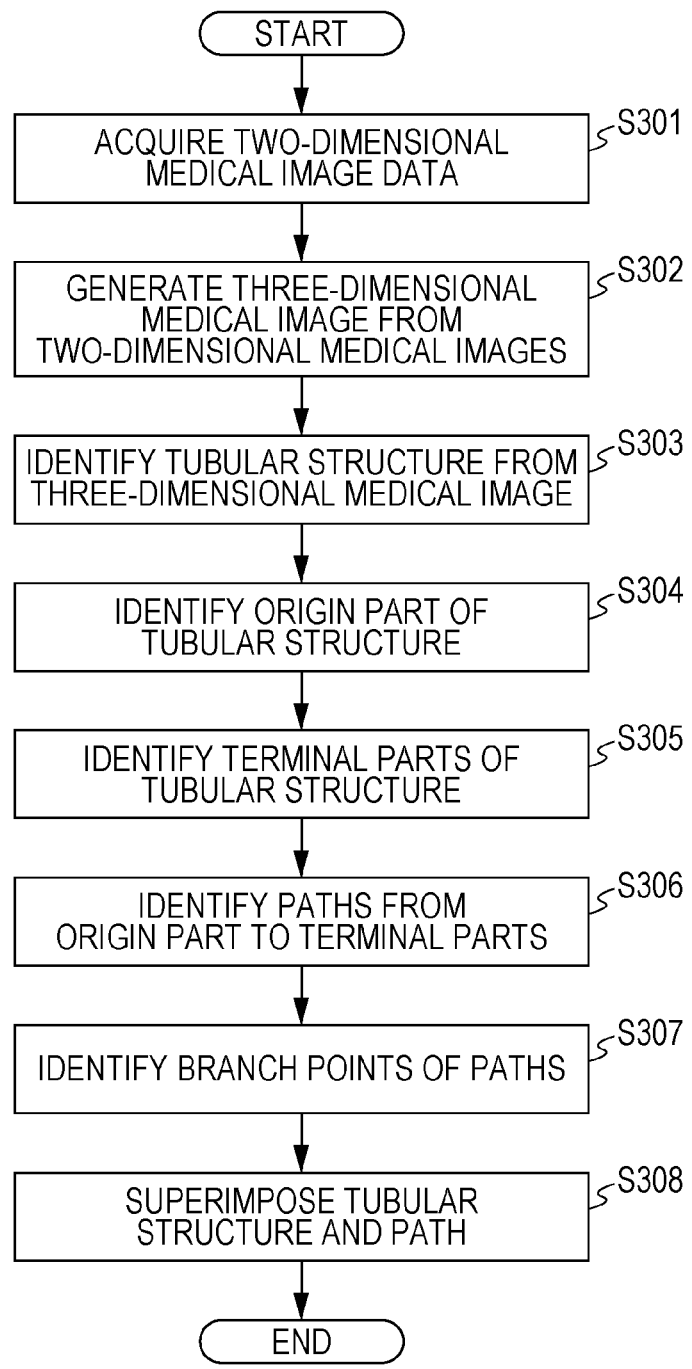
FIG. 3 is a flowchart illustrating an example of a flow of processing for analyzing a tubular structure.

FIG. 3 is a flowchart illustrating an example of a flow of processing for analyzing a tubular structure. Operations in steps S301 to S308 are executed by the CPU 101 in the medical image diagnosis apparatus 100. FIG. 3 illustrates details of the processing and the order of steps for illustration purpose only, and an embodiment of the present invention is not limited thereto.

In step S301, the image acquiring unit 200 acquires a plurality of two-dimensional medical images stored in the external memory 111. The image acquiring unit 200 may acquire a plurality of two-dimensional medical images output from a modality apparatus such as an X-ray CT apparatus or an MRI apparatus and stored in advance in the external memory 111 or may acquire them from a modality apparatus over a network. Alternatively, two-dimensional medical images designated by a user may be acquired, or medical images that are automatically selected may be acquired.

In step S302, the three-dimensional medical image generating unit 221 generates a three-dimensional medical image by using the plurality of two-dimensional medical images acquired in step S301. The three-dimensional medical image is generated by performing volume rendering on the plurality of two-dimensional medical images so that it can show a three-dimensional structure of the subject. The volume rendering performed here is based on a publicly known technology.

Figure 4:
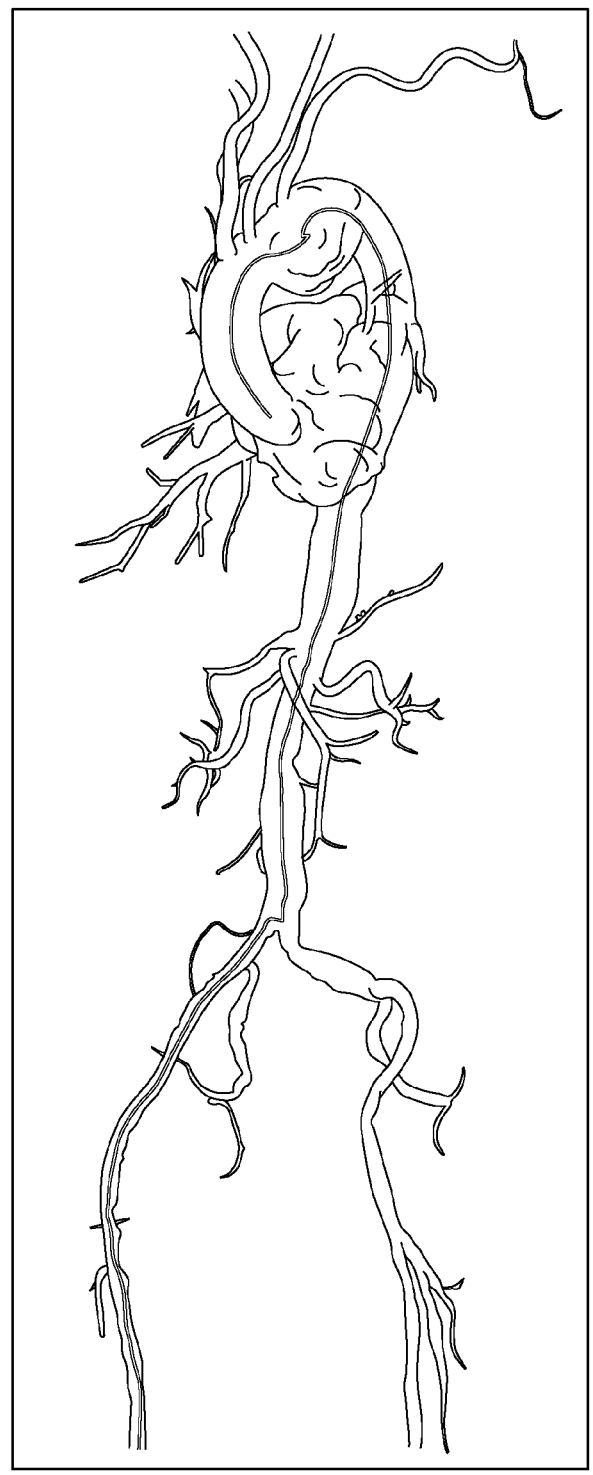
FIG. 4 illustrates an example of a tubular structure identified from a three-dimensional medical image.

In step S303, the tubular-structure identifying unit 241 identifies a tubular structure from the subject shown in the three-dimensional medical image generated in step S302. A tubular structure may be identified in the manner described above. FIG. 4 illustrates an example of a tubular structure identified in step S303. A necessary part may be extracted in accordance with an instruction from a user because there is a possibility that a logic for identifying a tubular structure may extract an unnecessary part.

In step S304, the origin part identifying unit 242 identifies an origin part of the tubular structure identified in step S303. An origin part may be identified in the manner as described above. The origin part according to this embodiment is an origin part of an aorta. Thus, the starting point of the aorta in vicinity of the heart is the origin part. The coordinates of the origin part on a three-dimensional space of the three-dimensional medical image are stored in an origin part information table 700 illustrated in FIG. 7.

The origin part information table 700 is stored in the external memory 111 or the RAM 103 and includes an item of origin-part coordinates 701. The origin-part coordinates 701 is an item under which coordinate values of the origin part identified in step S304 on the three-dimensional space are stored.

In step S305, the terminal part identifying unit 243 identifies terminal parts of the tubular structure identified in step S303. A terminal part may be identified in the manner as described above. A terminal part of this embodiment is a terminal part of each artery. Strictly speaking, the terminal parts correspond to capillary vessels, but, according to this embodiment, an end of a branch in the identified tubular structure is defined as a terminal part. The coordinates of the terminal parts on a three-dimensional space of the three-dimensional medical image are stored in a terminal part information table 710 illustrated in FIG. 7.

The terminal part information table 710 is stored in the external memory 111 or the RAM 103 and includes items of terminal part ID 711, terminal part coordinates 712, and terminal part distance 713. The terminal part ID 711 is an item under which identification information assigned to a terminal part is stored. The terminal part coordinates 712 is an item under which coordinate values of a terminal part on the three-dimensional space are stored. The terminal part distance 713 is an item under which a distance of a path from the origin part to a terminal part is stored. In step S305, the terminal part ID 711 and the terminal part coordinates 712 are stored.

Figure 5:
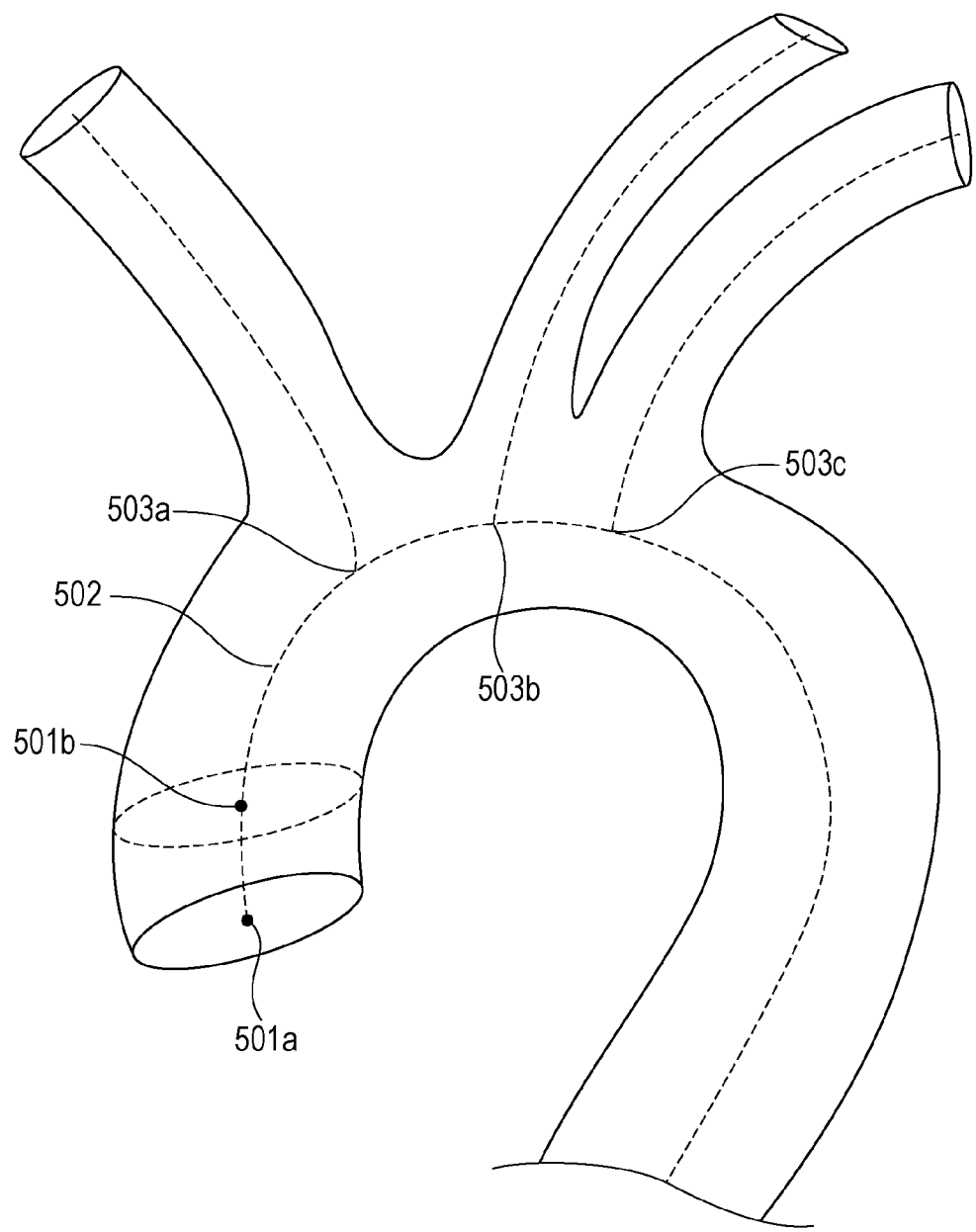
FIG. 5 illustrates an example of core lines of a tubular structure.

In step S306, the path identifying unit 244 identifies a core line from the origin part to each of the terminal parts of the tubular structure identified in step S303, and the identified core line is identified as a path to the terminal part. A path may be identified in the manner as described above. FIG. 5 schematically illustrates a tubular structure. FIG. 5 illustrates a center point (or center of gravity point) 501a and a center point (or center of gravity point) 501b of a vertical cross section against the axis direction of the tubular structure. The center points 501 are identified from the origin part to a terminal part, and the center points 501 are connected with each other to identify a core line 502. The core line is identified as a path to the terminal part. Coordinates of the path on a three-dimensional space of a three-dimensional medical image are stored in the path information table 720 illustrated in FIG. 7.

The path information table 720 is stored in the external memory 111 or the RAM 103 and includes items of path ID 721 and path coordinates 722. The path ID 721 is an item under which identification information assigned to a path is stored. The path coordinates 722 is an item under which coordinate values of the center point 501 forming a path on a three-dimensional space are stored.

Furthermore, after the path from the origin part to the terminal part is identified, the distance identifying unit 246 identifies the distance of the path from the origin part to the terminal part. The identified distance is stored in the terminal part distance 713. The path corresponding to a terminal part can be identified from the path coordinates 722 including the coordinate values stored in the terminal part coordinates 712.

In step S307, the branch-point identifying unit 245 identifies a branch point of the path identified in step S306. As illustrated in FIG. 5, the branching tubular structure has branch points 503. FIG. 5 illustrates three branch points of a branch point 503a, a branch point 503b, and a branch point 503c. These parts as described above may be identified by a publicly known technology. The distance identifying unit 246 identifies the distance of the path from the origin part to each of the branch points. The coordinates and distance relating to a branch point on the three-dimensional space of the three-dimensional medical image are stored in a branch point information table 730 illustrated in FIG. 7.

The branch point information table 730 is stored in the external memory 111 or the RAM 103 and includes items of branch point ID 731, branch point coordinates 732, and branch point distance 733. The branch point ID 731 is an item under which identification information assigned to a branch point is stored. The branch point coordinates 732 is an item under which coordinate values of a branch point on the three-dimensional space are stored. The branch point distance 733 is an item under which the distance of a path from the origin part to a branch point is stored.

Figure 6:
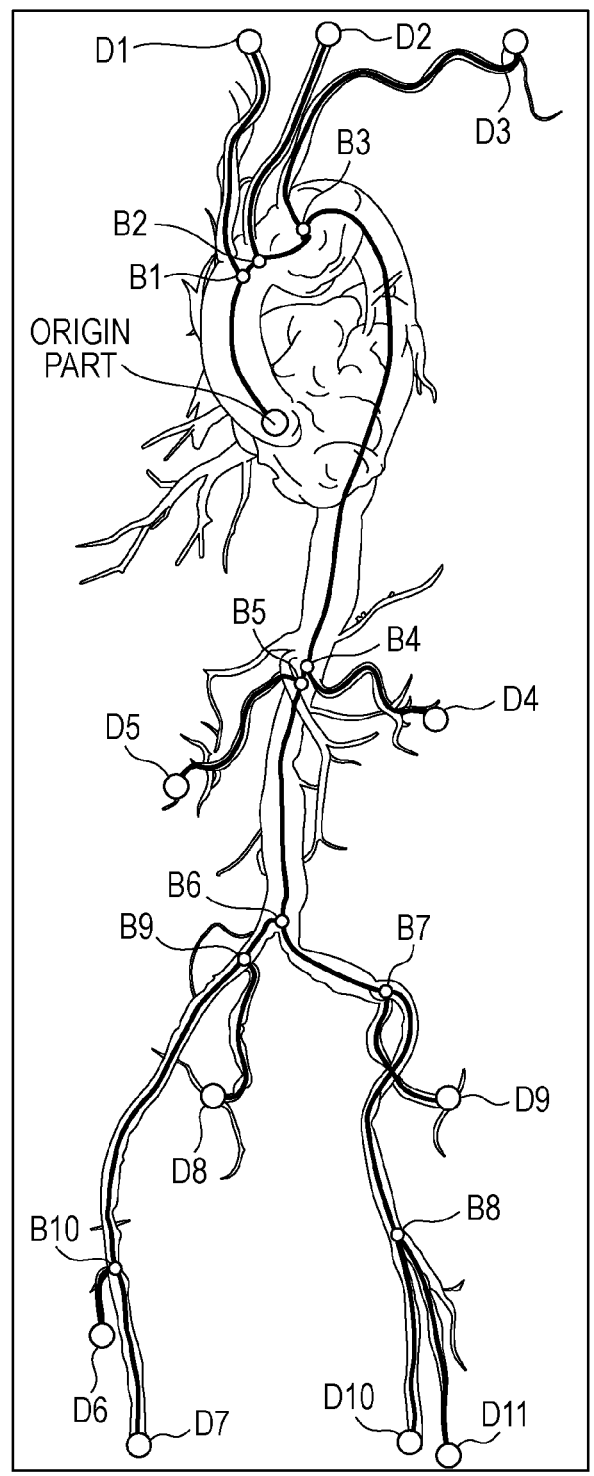
FIG. 6 illustrates examples of regions of origin, terminal parts, branch points, and paths of a tubular structure.

In step S308, the display unit 231 displays the tubular structure identified in step S303 as illustrated in FIG. 4 on the display 110 and superimposes the origin part, terminal parts, paths, branch points identified in steps S304 to S307. FIG. 6 illustrates a result of the superimposition of them on the tubular structure. Because the coordinate values indicative of the parts as described above are identified in steps S304 to S307, the coordinate values are acquired from the corresponding tables in FIG. 7. Then, the parts are superimposed based on the coordinate values. FIG. 6 illustrates the parts along with their names and IDs. The following descriptions are based on the IDs in FIG. 6.

Figure 8:
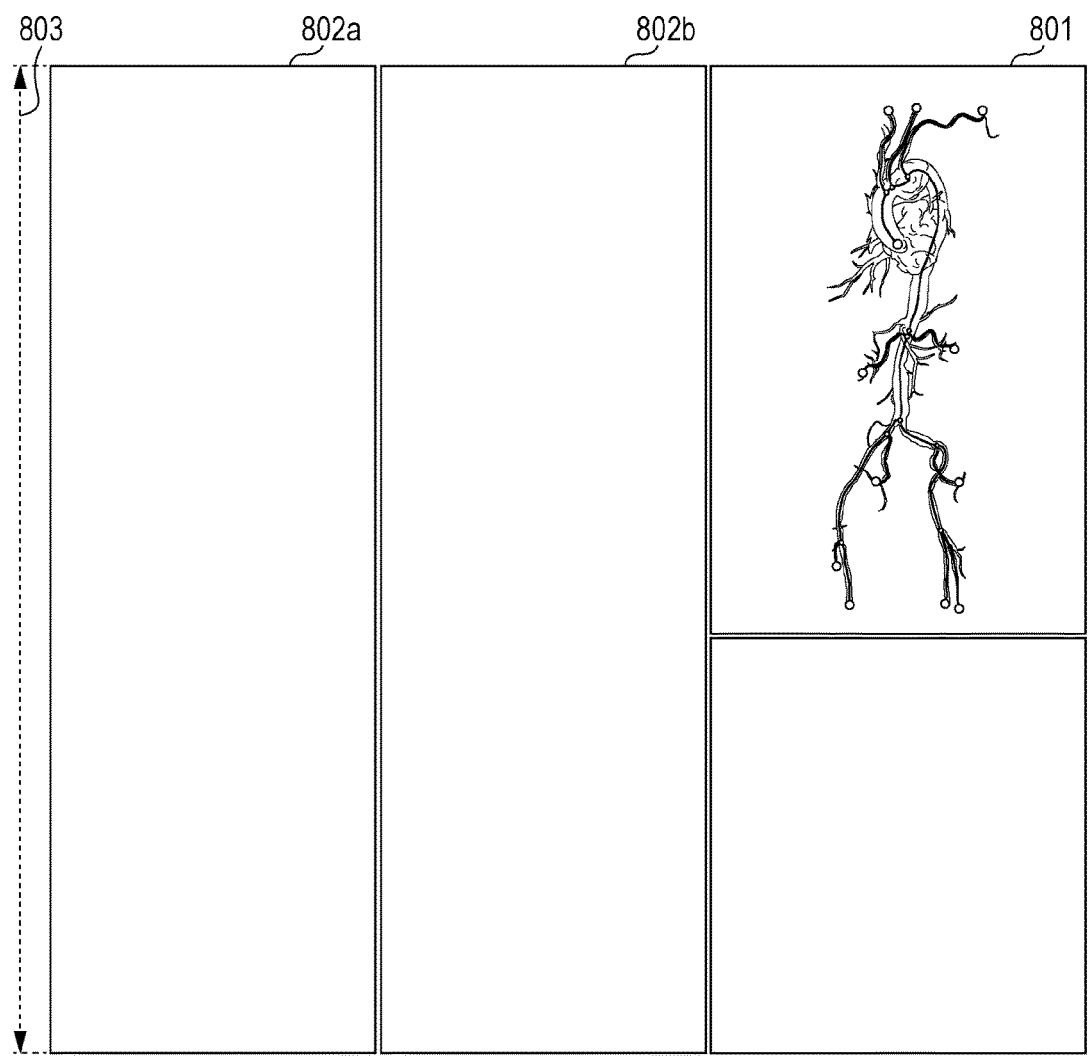
FIG. 8 illustrates an example of a screen configuration of a CPR image comparison screen.

The display unit 231 may generate a CPR image comparison screen illustrated in FIG. 8 as a window of an application for a diagnosis based on a medical image and may display it on the display 110. The CPR image comparison screen includes a tubular structure display area 801 and a CPR image display area 802. In tubular structure display area 801, the identified tubular structure and the identified origin part, terminal parts, paths, and branch points are superimposed. In the CPR image display area 802, a CPR image generated by a process, which will be described below, is displayed for each terminal part or path. The CPR image display area 802 will be described as a display area displaying a part of a CPR image according to this embodiment, but an embodiment of the present invention is not limited thereto. Providing the tubular structure display area 801 and the CPR image display area 802 in one window can eliminates the necessity for displaying a plurality of windows. Thus, operations can be performed efficiently. The following description will be based on the CPR image comparison screen.

Next, with reference to FIGS. 9 to 12, a flow of processing for displaying a CPR image will be described.

FIG. 9 is a flowchart illustrating an example of a flow of processing for displaying a CPR image from an origin part to a selected terminal part of a tubular structure. The operations in steps S901 to S910 are executed by the CPU 101 in the medical image diagnosis apparatus 100. The details of processing and the order of operations are given in FIG. 9 for illustration purpose only, and an embodiment of the present invention is not limited thereto.

In step S901, the operation receiving unit 210 determines whether a selection of a terminal part of the tubular structure displayed in the tubular structure display area 801 is received or not. In other words, whether a selection of one of the terminal parts D1 to D11 illustrated in FIG. 6 is received or not is determined. If it is determined that a selection of a terminal part is received, the processing proceeds to step S902. If not, the processing waits without proceeding to step S902.

In step S902, the path identifying unit 244 identifies the path corresponding to the terminal part for which the selection has been received. The terminal part coordinates 712 of the terminal part for which the selection has been received are identified, and the path indicated by the path coordinates 722 including the coordinate values is the path corresponding to the terminal part. According to this embodiment, a path from the origin part to a terminal part is identified in advance, and the path corresponding to the terminal part is identified in response to a selection for a terminal part. However, the path from the origin part to the terminal part for which the selection has been received may be traced in response to the selection for the terminal part.

In step S903, the distance identifying unit 246 identifies the length of a longer side of the CPR image display area 802 displaying a CPR image generated by processing which will be described below. The CPR image display area 802 has a longer side 803 in FIG. 8. In step S903, the pixel value of the length is identified.

Figure 10A:
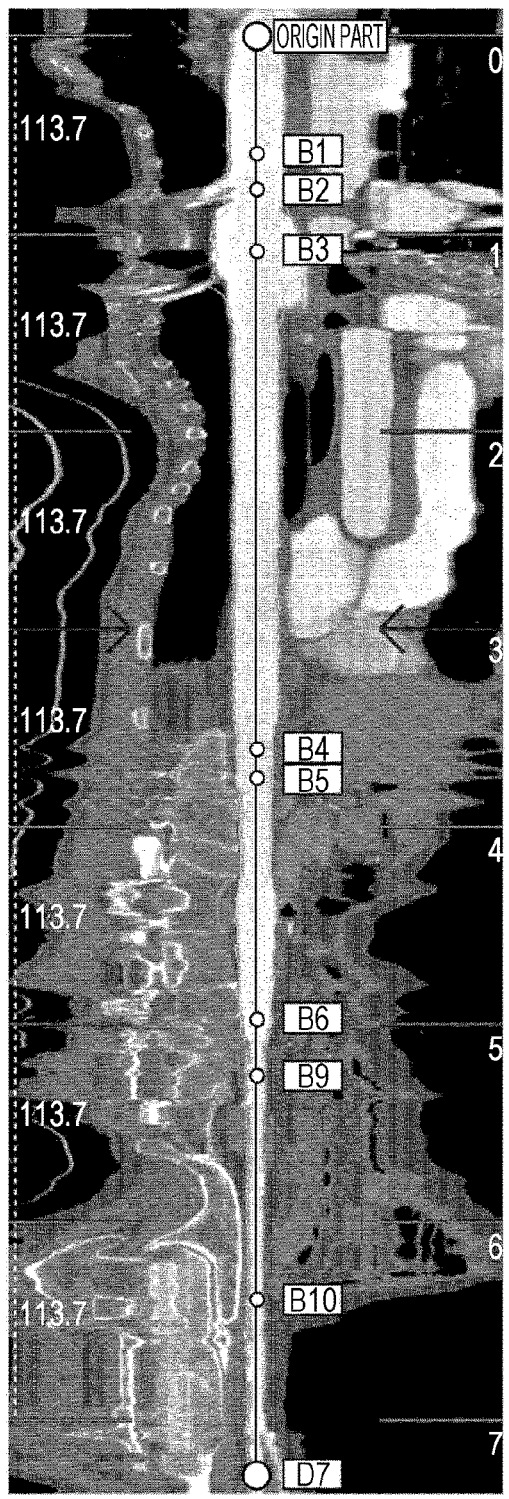
FIGS. 10A and 10B illustrate examples of a CPR image showing a path from an origin part to a terminal part and a CPR image showing a show from the origin part to another terminal part.
Figure 10B:
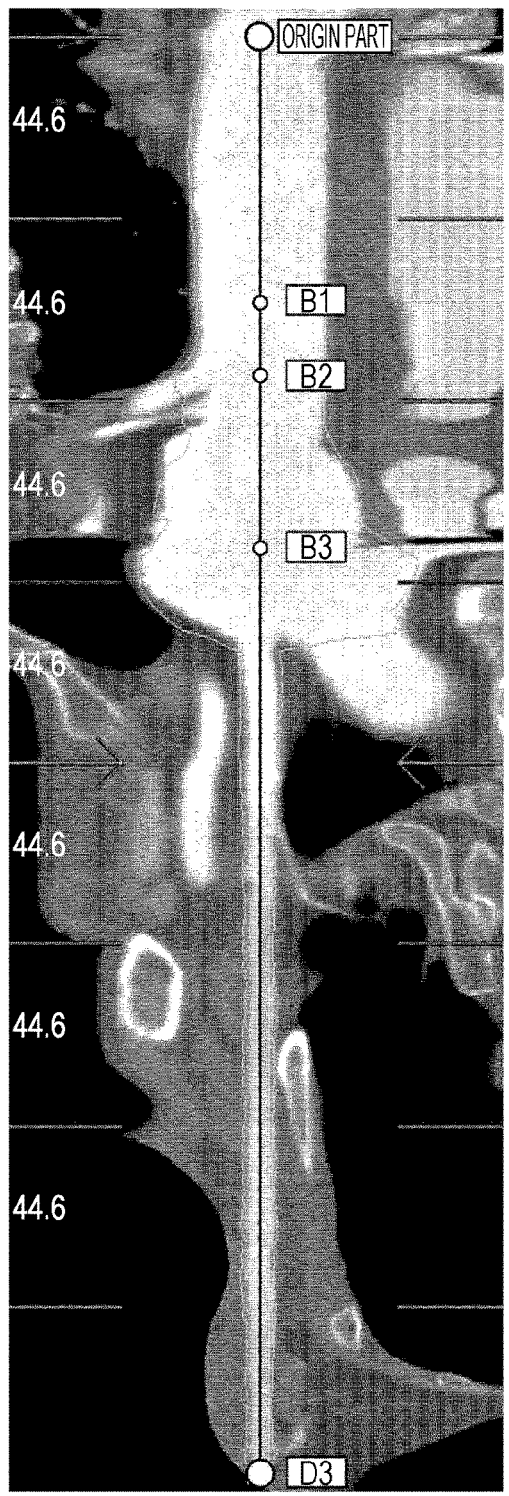

In step S904, the CPR image generating unit 222 generates a CPR image of the path identified in step S902 by using the length identified in step S903. The CPR image is generated by using a publicly known technology. For example, Japanese Patent Laid-Open Nos. 2004-283373, 2011-206155, and 2012-24517 may be referred. By following such a well known algorithm, a cross-sectional curved surface is set which is a curved surface including a core line indicating the path, which is taken from the tubular structure along the longitudinal direction. The cross-sectional curved surface is projected to generate a CPR image. According to the algorithm which projects a cross-sectional curved surface, the CPR image is generated such that the longer side can have the length identified in step S903. Thus, the generated CPR image does not have an excessively small size, which is easily viewable by a user. The generated CPR image may be a straightened CPR image. Because a straightened CPR image shows the section from the origin part to the terminal part of the tubular structure in an enlarged size as illustrated in FIGS. 10A and 10B, the tubular structures can be easily compared.

In step S905, the display control unit 230 determines whether a CPR image showing another path different from the path identified in step S902 is displayed in the CPR image display area 802 or not. If it is determined that the CPR image showing another path is displayed, the processing moves to step S907. If not, that is, if it is determined that no CPR image showing a path is displayed in the CPR image display area 802, the processing moves to step S906.

Figure 7:
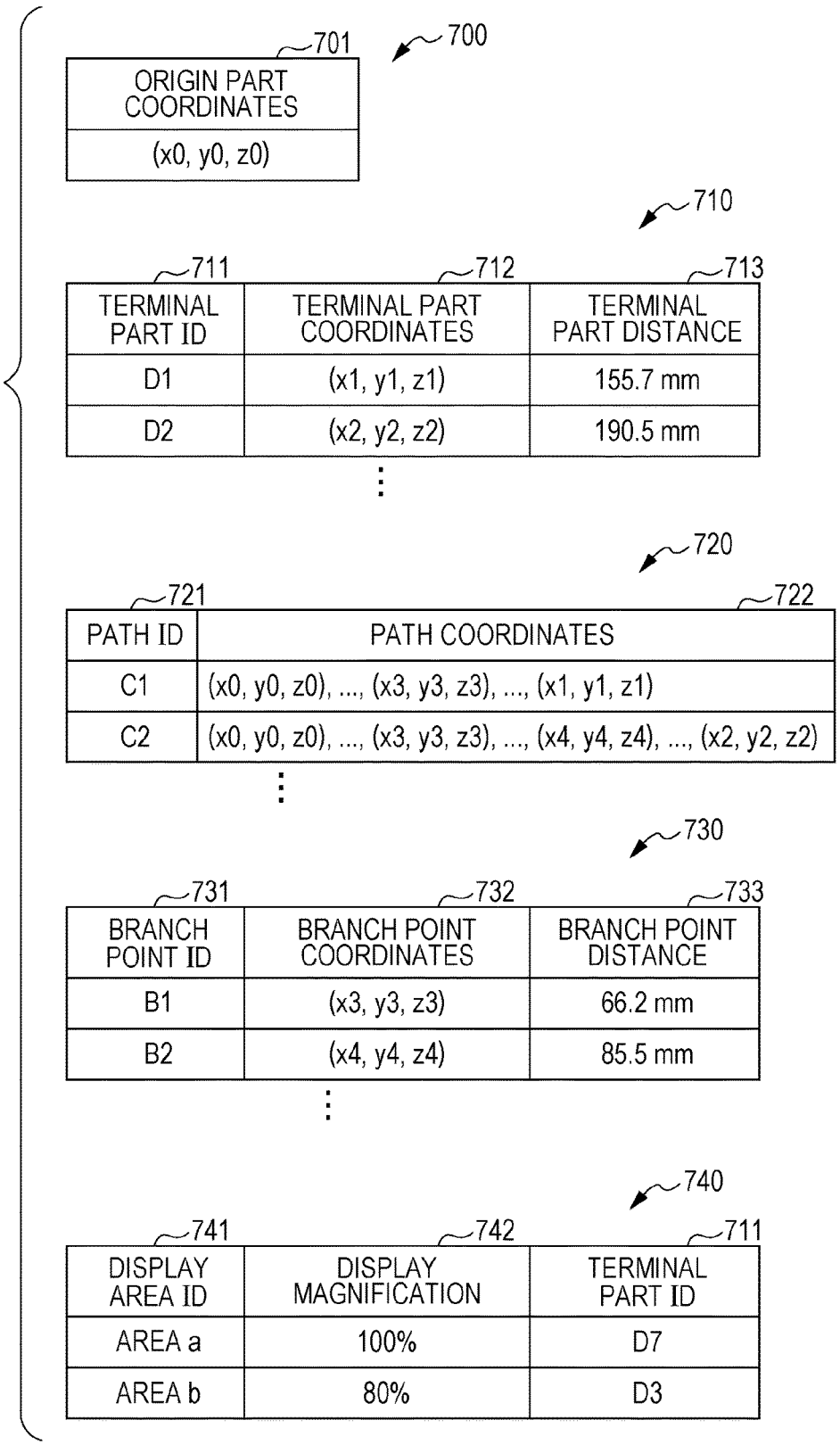
FIG. 7 illustrates examples of table configurations of tables.

In step S906, the display unit 231 causes the CPR image generated in step S904 showing the path from the origin part of the tubular structure to the terminal part of the tubular structure including branch points to be displayed in the CPR image display area 802. A display area information table 740 as illustrated in FIG. 7 is first referred, and the CPR image display area 802 for displaying the CPR image generated in step S904 is determined based on a display area ID 741 in the display area information table 740 in which a terminal part ID 711 is vacant. Then, the CPR image generated in step S904 is displayed in the determined CPR image display area 802. The display magnification is initially set to 100%.

The display area information table 740 is stored in the external memory 111 or the RAM 103 and includes items of display area ID 741, display magnification 742, and terminal part ID 711. The display area ID 741 is an item under which identification information assigned to each CPR image display area 802 is stored. The display magnification 742 is an item under which a display magnification of a CPR image to be displayed in the CPR image display area 802 is stored. The terminal part ID 711 is an item under which the terminal part ID 711 corresponding to a CPR image to be displayed in the CPR image display area 802 is stored. The terminal part ID 711 corresponds to the terminal part ID 711 in the terminal part information table 710. The display area information table 740 is updated every time a CPR image is displayed. In step S906, under the terminal part ID 711 in the display area information table 740, the terminal part ID (terminal part ID 711 in the terminal part information table 710) corresponding to the path of the CPR image to be displayed is stored at a record corresponding to the CPR image display area 802.

The origin parts, branch points, and terminal parts are indicated by corresponding icons on the display such that paths included in the CPR image can be identified. The icons corresponding to the parts are displayed at display positions determined based on the information (such as distance from the origin part and coordinates) illustrated in FIG. 7. The display positions are adjusted such that a path included in the CPR image can be displayed near the center of the CPR image display area 802.

Figure 11:
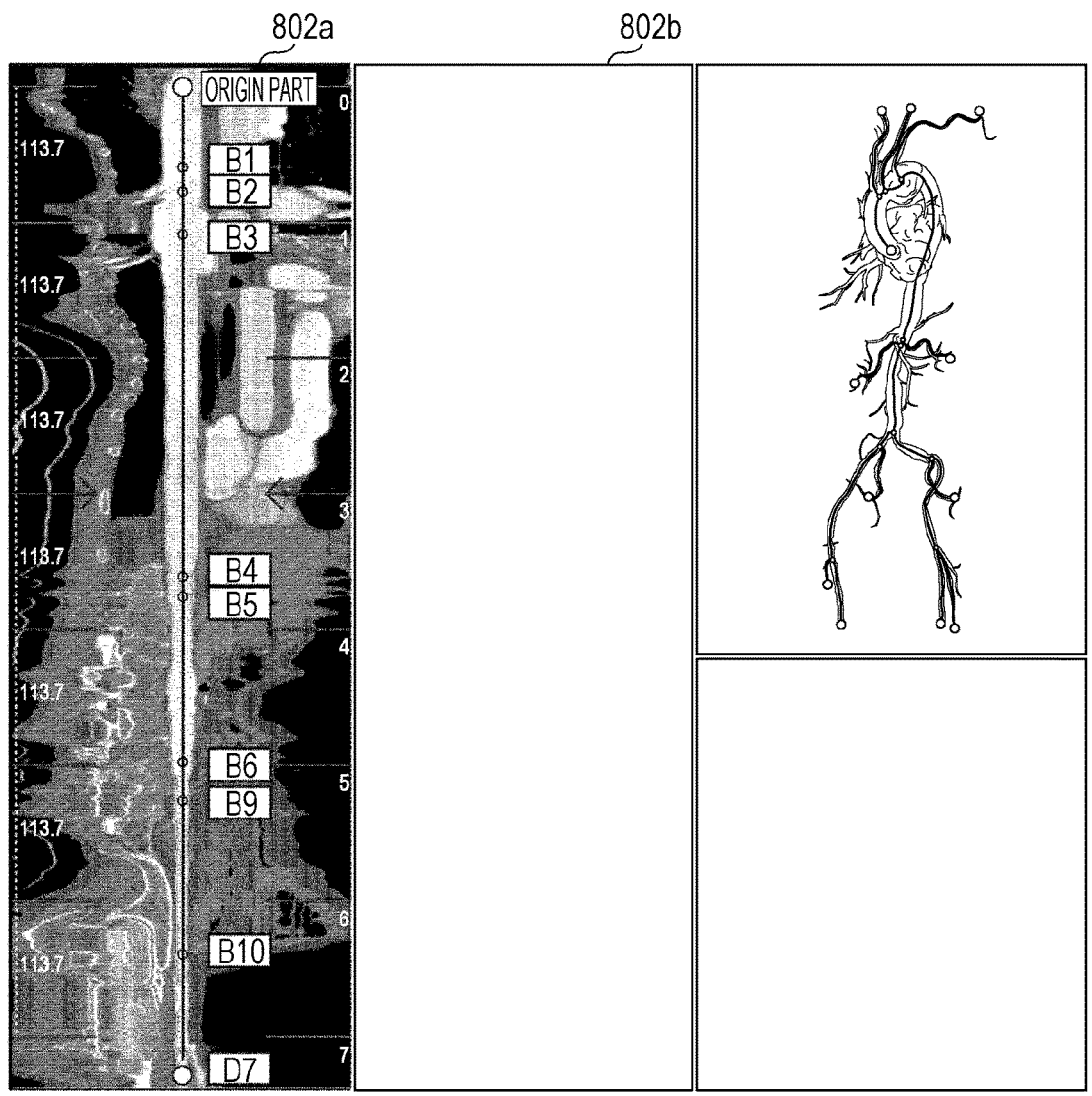
FIG. 11 illustrates an example of a CPR image comparison screen displaying a CPR image showing a path from an origin part to a terminal part.

FIG. 11 illustrates an example of a CPR image displayed in the manner described above. According to this embodiment, because there are two CPR image display areas 802 on the CPR image comparison screen, a CPR image generated for the first time (such as the CPR image from the origin part to the terminal part D7 illustrated in FIG. 10A) is displayed in the CPR image display area 802a. The display area to display such a CPR image may be determined automatically, or such a CPR image may be displayed in a display area designated by a user.

On the other hand, in step S907, the branch-point identifying unit 245 identifies an identical branch point between the path identified in step S902 and the other path corresponding to the CPR image being displayed. The path coordinates 722 of the paths are acquired, and the acquired path coordinates 722 are compared. Thus, because identical paths can be identified among the paths, the branch points included in the identical path are identified from the branch point coordinates 732. The branch point corresponding to the identified branch point coordinates 732 is an identical branch point between the paths. For example, three branch points B1, B2 and B3 are identical branch points identified between the two paths illustrated in FIGS. 10A and 10B (on the CPR image from the origin part to the terminal part D7 illustrated in FIG. 10A and the CPR image from the origin part to the terminal part D3 illustrated in FIG. 10B).

In step S908, the branch-point identifying unit 245 identifies positions (coordinate positions on the images) of the branch points identified in step S907 and the origin part on the CPR images. More specifically, the branch-point identifying unit 245 identifies the positions of the branch points and the origin part on the CPR image being displayed and the positions of the branch points and the origin part on the CPR image generated in step S904. With respect to the branch points, the position of one of the branch points may be identified in step S907.

Figure 24:
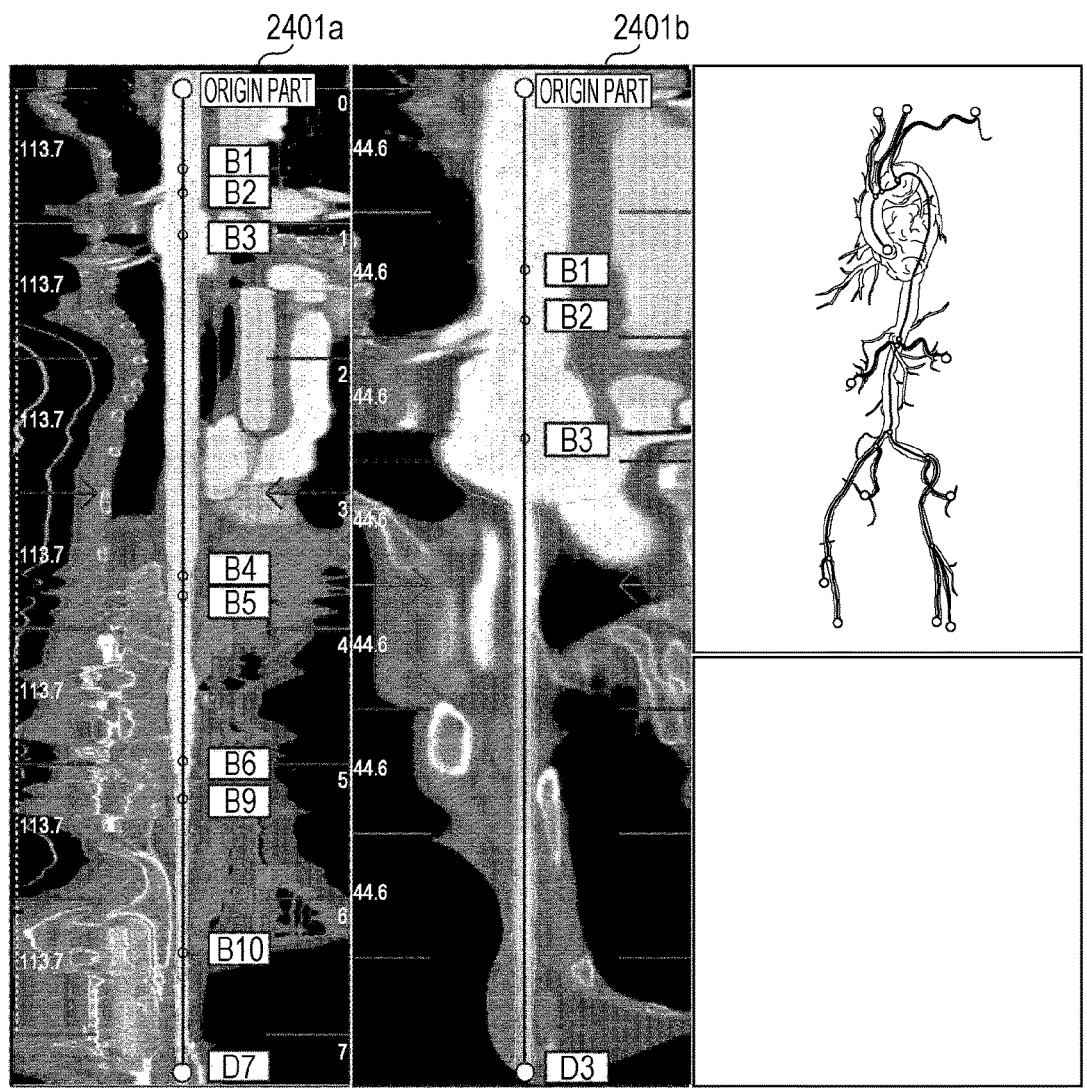
FIG. 24 illustrates an example of CPR images generated and displayed in accordance with the length of the longer side of a CPR image display area.

In step S909, the display magnification determining unit 232 determines the display magnification for the CPR image generated in step S904 in accordance with the positions of the branch point and origin part identified in step S908. The images illustrated in FIGS. 10A and 10B will be described, for example. Directly displaying the branch point B1 on the CPR image (FIG. 10B) generated in step S904 and the branch point B1 on the CPR image (FIG. 10A) being displayed results in the images displayed in the CPR image display areas 802 as illustrated in FIG. 24. As illustrated in FIG. 24, on the resulting images, the heights of the identical branch points (branch point B1, branch point B2, and branch point B3) (or the lengths from the origin part to the branch points on the CPR image) are not equal. Accordingly, the display magnification is determined such that the heights can be matched with the position of the branch point identified in step S908. For example, in a case where the height of the branch point B1 in FIG. 10A is 50 and the height of the branch point B1 in FIG. 10B is 100, the height of the branch point B1 in FIG. 10B is 50 where the display magnification is 50%. Thus, the display magnification is determined as 50% in step S909.

More specifically, the distance from the origin part of a first path being displayed to a branch point (identical to a branch point of a second path) of the first path on a CPR image is identified. Next, the distance from the origin part of the second path to be displayed to the branch point (identical to the branch point of the first path) of the second path on a CPR image is identified. Then, the identified distances are compared, and the display magnification for the second path is calculated such that the branch point of the first path and the branch point of the second path can be at an equal distance, that is, at an identical height on the CPR images. The calculated result is determined as the display magnification for the second display path. According to this embodiment, an origin part and a common branch point are used to determine the display magnification. However, a plurality of common branch points if any may be used instead of the origin part. For example, because the branch point B1 and the branch point B2 are common between the path in FIG. 10A and the path in FIG. 10B, the distance from the branch point B1 to the branch point B2 may be determined from the CPR images to acquire the display magnification.

In step S910, the display unit 231 displays the CPR image generated in step S904 at the display magnification determined in step S909 in the CPR image display area 802. The display area information table 740 is referred, and if there is any free CPR image display area 802, a CPR image generated at the oldest date and time is deleted. The resulting free CPR image display area 802 is determined to be used for the display. Alternatively, a new CPR image display area 802 may be provided. Then, under the terminal part ID 711 in the display area information table 740, the terminal part ID (terminal part ID 711 in the terminal part information table 710) corresponding to the path of the CPR image to be displayed is stored at a record corresponding to the CPR image display area 802. Furthermore, the display magnification determined in step S909 is stored under the display magnification 742 of the record. Thus, the generated CPR image is displayed at the display magnification determined in the determined CPR image display area 802.

Figure 12:
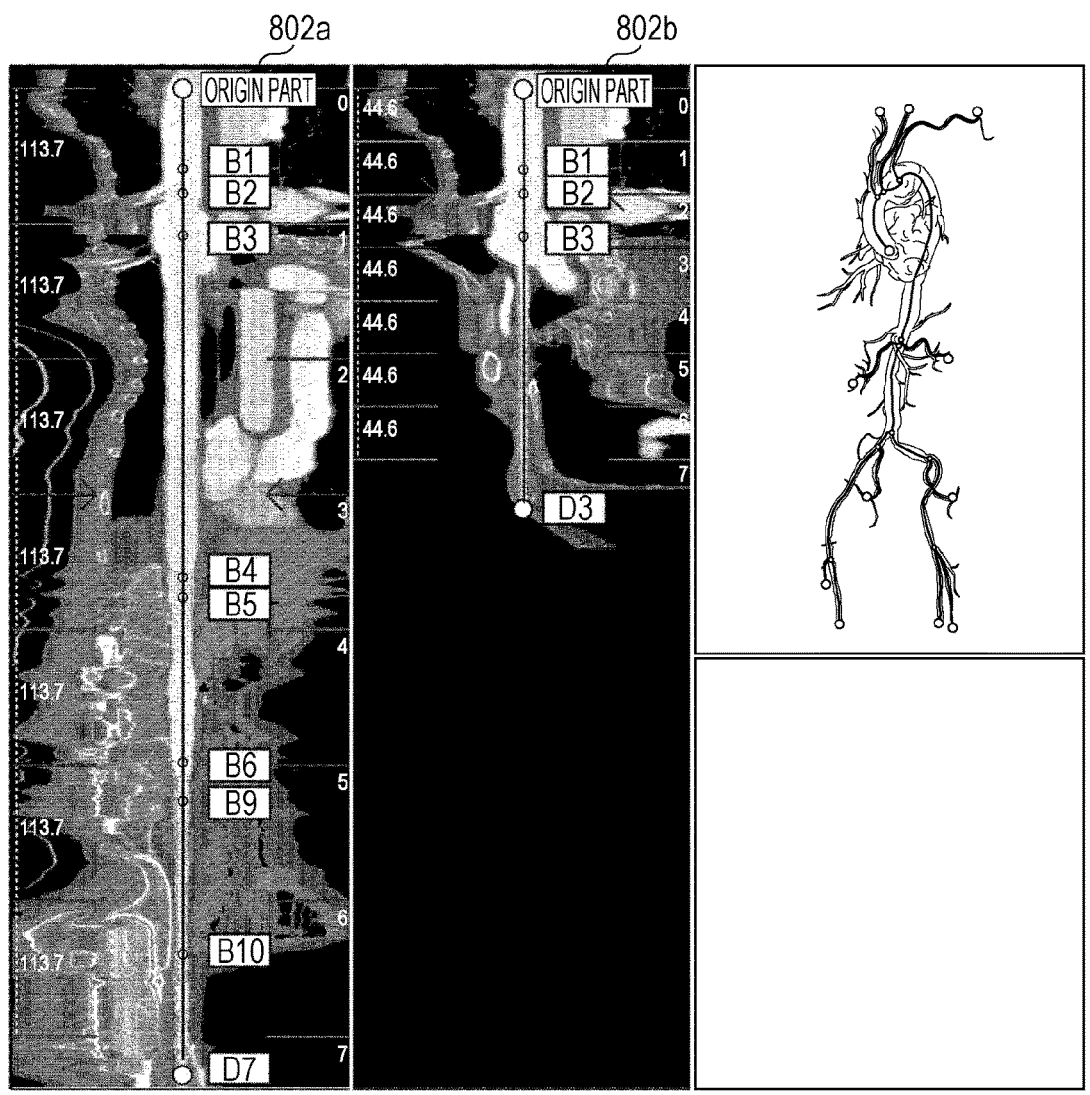
FIG. 12 illustrates an example of a CPR image comparison screen displaying a CPR image showing a path from an origin part to a terminal part and a CPR image showing a path from the origin part to another terminal part.

According to this embodiment, the size (longitudinal and latitudinal pixel values) of the CPR image may be maintained while the display magnification is changed. However, the size of the CPR image may also be changed. In this way, displaying the images at a display magnification changed such that identical branch points can be at an equal height results in images illustrated in FIG. 12. FIG. 12 illustrates a case where a new CPR image (showing from the origin part to the terminal part D3 in FIG. 10B) is displayed in the CPR image display area 802b of the CPR image comparison screen illustrated in FIG. 11. These two CPR images (the CPR image from the origin part to the terminal part D7 illustrated in FIG. 10A and the CPR image from the origin part to the terminal part D3 illustrated in FIG. 10B) show two paths identical to those in FIG. 24. The display magnification determined in step S909 is used to display the CPR image generated in step S904 so that the height of the branch point identical to a branch point of another path can be equal to the height of the branch point of the other path.

Next, with reference to FIG. 13 and FIG. 14, a flow of processing for changing display magnifications of CPR images will be described.

Figure 13:
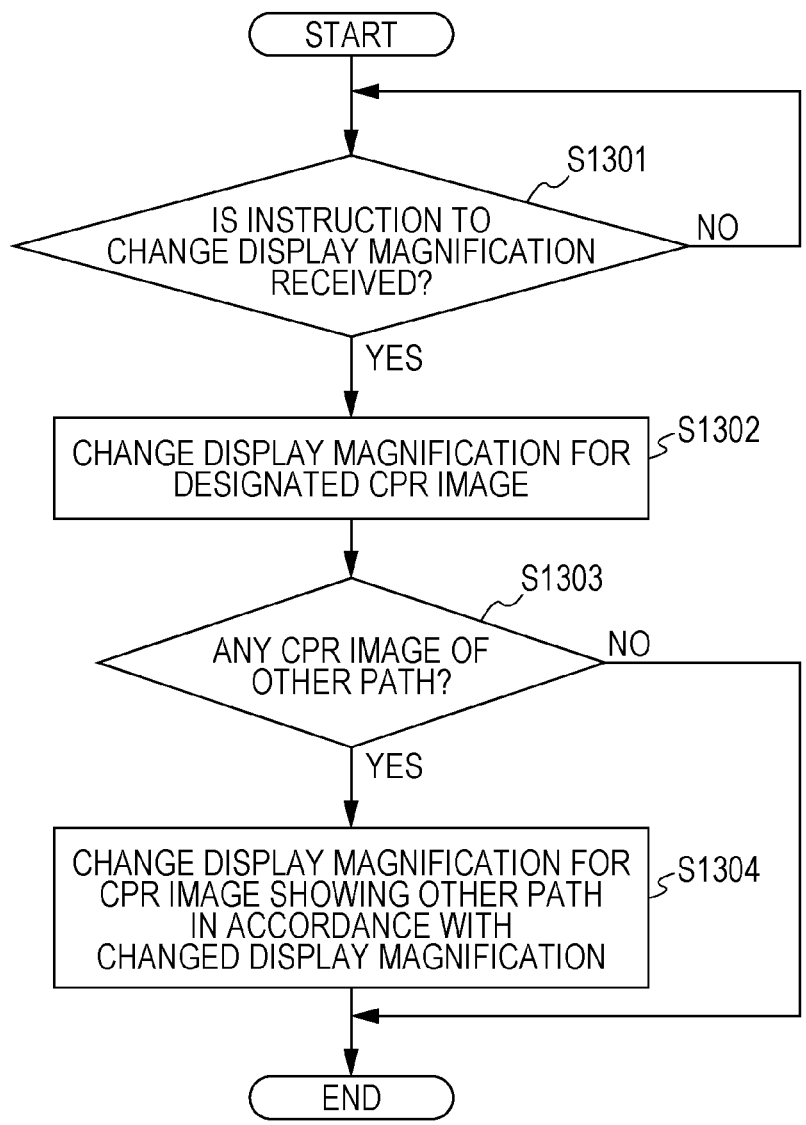
FIG. 13 is a flowchart illustrating an example of a flow of processing for changing the display magnification of a CPR image to be displayed in a CPR image display area.
Figure 14:
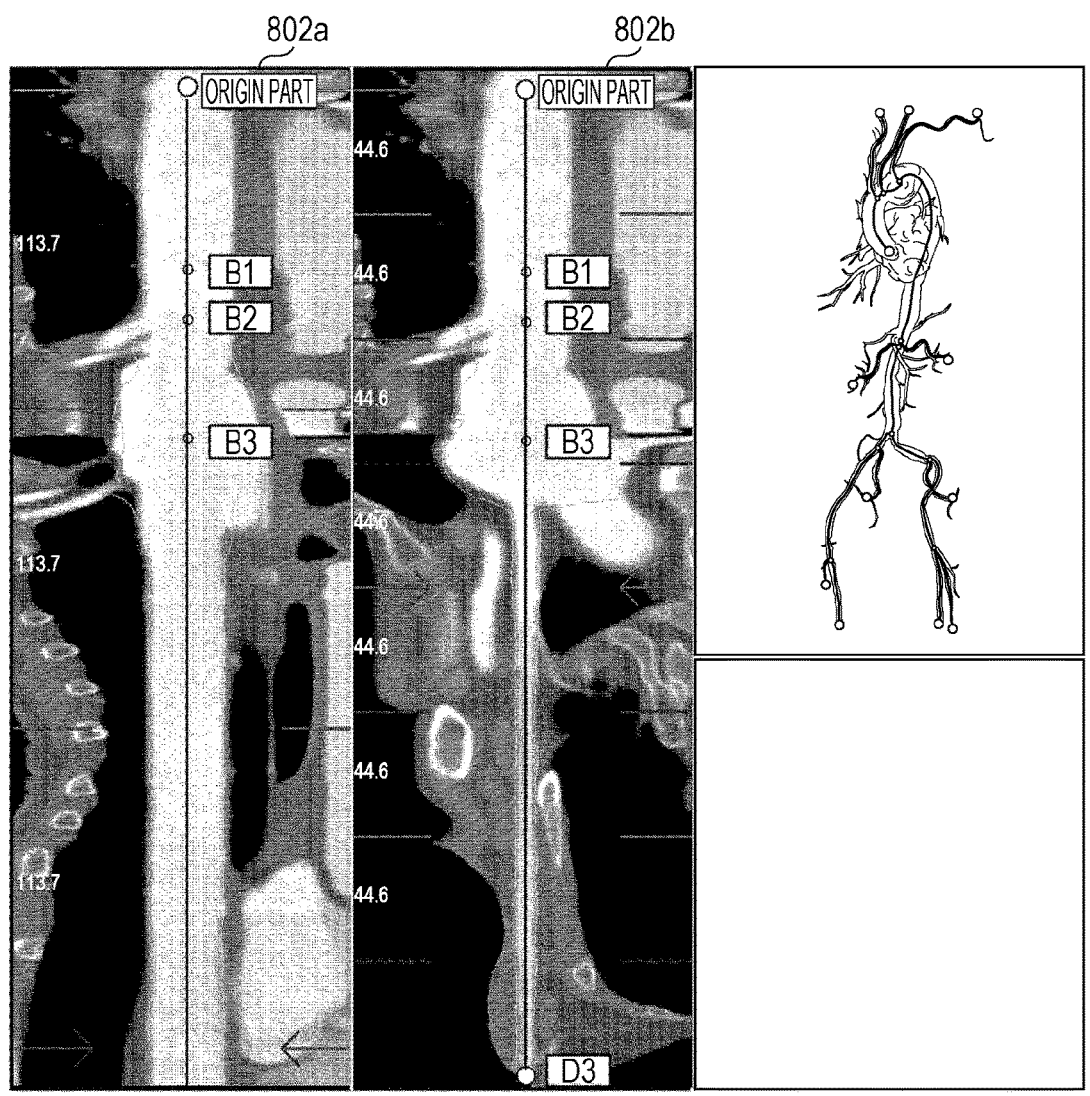
FIG. 14 illustrates an example of a result of a change of the display magnification of the CPR image displayed in the CPR image display area.

FIG. 13 is a flowchart illustrating an example of a flow of the processing for changing the display magnification for a CPR image to be displayed in the CPR image display area 802. The operations in steps S1301 to step S1304 are executed by the CPU 101 in the medical image diagnosis apparatus 100. The details of processing and the order of operations are given in FIG. 13 for illustration purpose only, and an embodiment of the present invention is not limited thereto.

In step S1301, the operation receiving unit 210 determines whether an instruction to change the display magnification for one of CPR images to be displayed in the CPR image display areas 802 is received or not. If it is determined that an instruction to change the display magnification is received, the processing proceeds to step S1302. If not, the processing waits without proceeding to step S1302.

In step S1302, the display unit 231 changes the display magnification 742 for the CPR image instructed from a user to the display magnification instructed by the user. Thus, the size of the CPR image can be enlarged or reduced to be displayed in the CPR image display area 802.

In step S1303, the display control unit 230 determines whether a CPR image showing another path different from the path shown in the CPR image designated by the user is being displayed in the CPR image display area 802 or not. If it is determined that the CPR image showing another path is being displayed, the processing moves to step S1304. If it is not determined that the CPR image showing another path is displayed, that is, if it is determined that no CPR image showing a path is displayed in the CPR image display area 802, the processing ends.

In step S1304, the display unit 231 changes the display magnification 742 for the CPR image showing the other path in accordance with the display magnification 742 changed in step S1302. For example, when the display magnification 742 is changed from 100% to 50% in step S1302 and the CPR image showing the other path is displayed at 40%, the display magnification is ½. Therefore, the display magnification of the CPR image showing the other path is also equal to 20% which is ½. As described above, even when the display magnifications are adjusted such that identical branch points can be displayed at an equal height, the display magnification of the other CPR image can be changed in interlocking manner so as to keep their equal heights. FIG. 14 illustrates an example of a case where the display magnification is changed in step S1302 and step S1304. In the case illustrated in FIG. 14, the display magnification of the CPR image being displayed in the CPR image display area 802a is changed among the CPR images illustrated in FIG. 12. When the display magnification of the CPR image being displayed in the CPR image display area 802a is changed, the display magnification of the CPR image being displayed in the CPR image display area 802b is also changed in interlocking manner. Thus, the sizes of the images are enlarged or reduced by keeping the heights of identical branch points equal as illustrated in FIG. 14.

Next, with reference to FIGS. 15 and 16, a flow of processing for changing the display positions of CPR images will be described.

Figure 15:
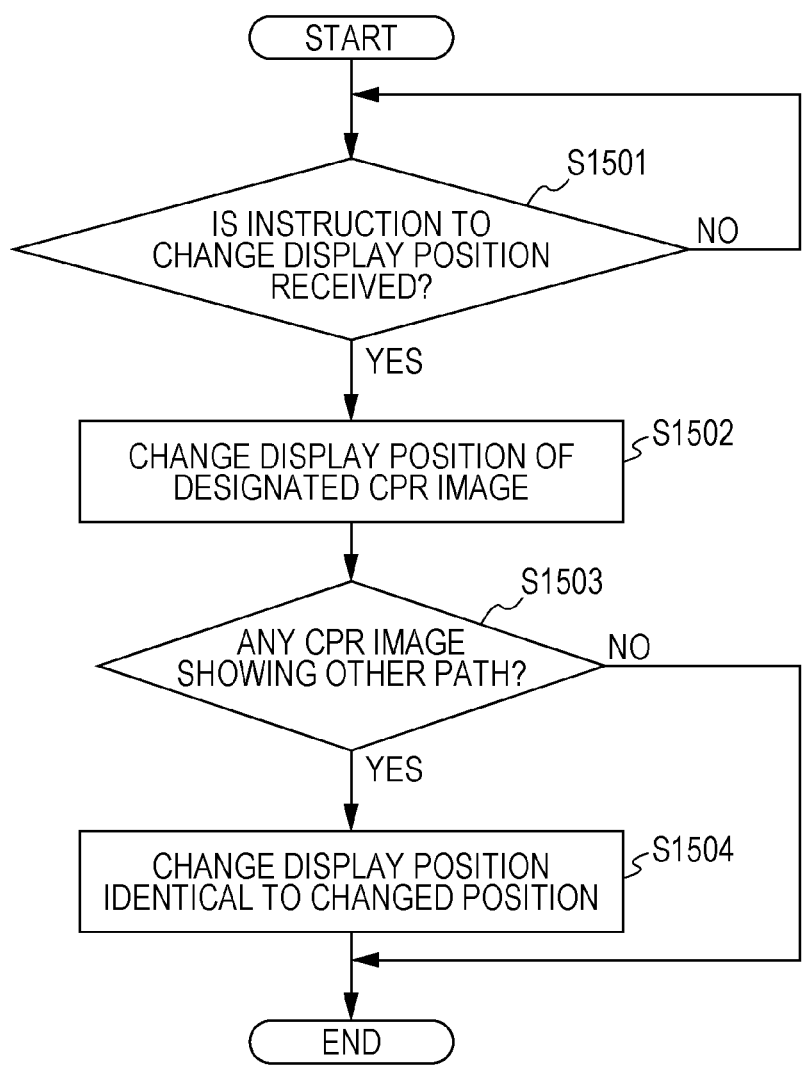
FIG. 15 is a flowchart illustrating an example of a flow of processing for changing the display position of a CPR image displayed in the CPR image display area.
Figure 16:
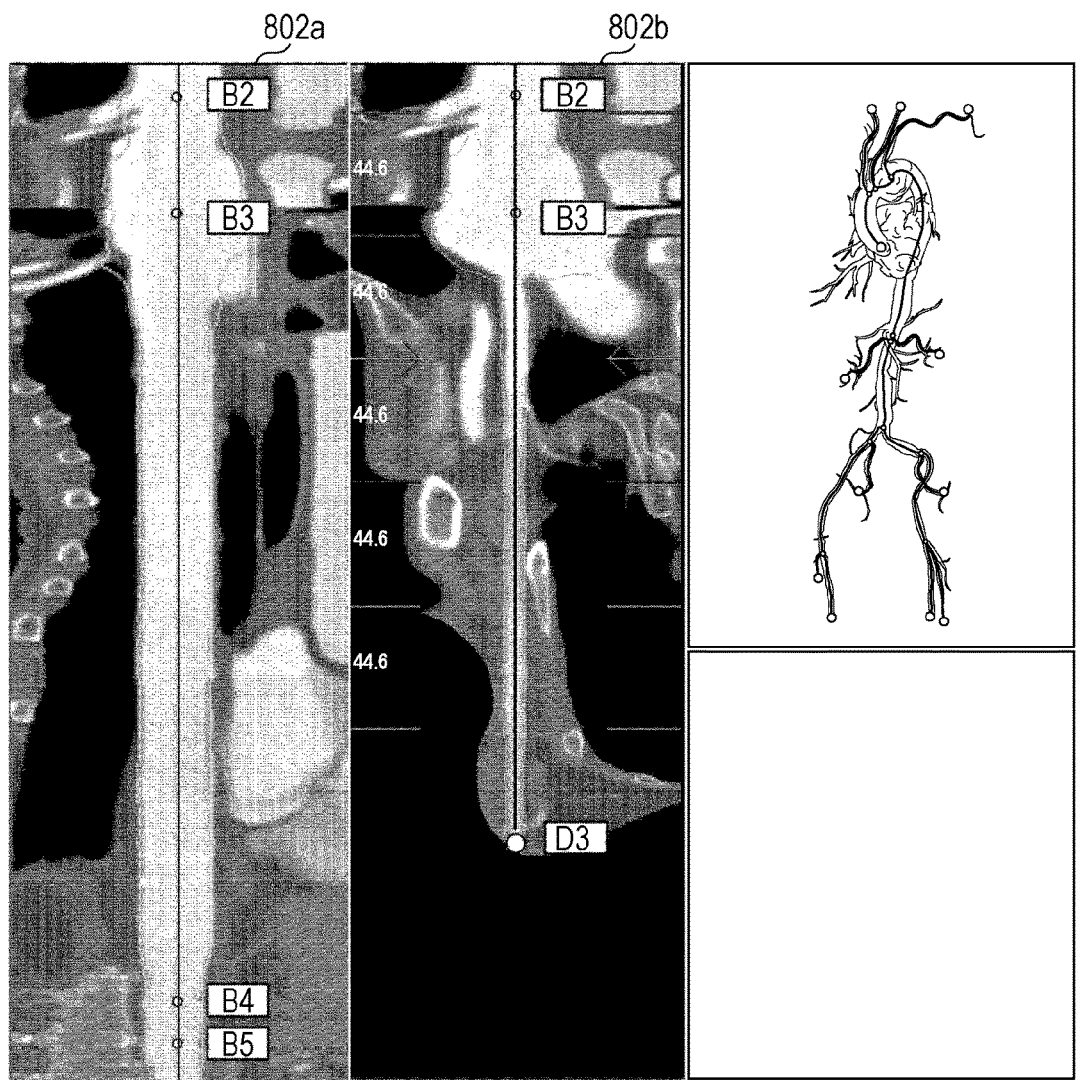
FIG. 16 illustrates an example of a result of the change of the display position of a CPR image displayed in the CPR image display area 802.

FIG. 15 is a flowchart illustrating an example of a flow of processing for changing the display positions of CPR images to be displayed in the CPR image display areas 802. The operations in steps S1501 to S1504 are executed by the CPU 101 in the medical image diagnosis apparatus 100. The details of processing and the order of operations are given in FIG. 15 for illustration purpose only, and an embodiment of the present invention is not limited thereto.

In step S1501, the operation receiving unit 210 determines whether an instruction to change the display position of one of the CPR images to be displayed in the CPR image display areas 802 is received or not. It if is determined that an instruction to change the display position is received, the processing proceeds to step S1502. If not, the processing waits without proceeding to step S1502.

In step S1502, the display unit 231 changes the display position of the CPR image instructed by a user to the display position instructed by the user. Thus, the CPR image which does not fully fit into the CPR image display area 802 can be displayed.

In step S1503, the display control unit 230 determines whether a CPR image showing another path different from the path shown in the CPR image designated by the user is being displayed in the CPR image display area 802 or not. If it is determined that the CPR image showing another path is being displayed, the processing moves to step S1504. If it is not determined that the CPR image showing another path is displayed, that is, if it is determined that no CPR image showing a path is displayed in the CPR image display area 802, the processing ends.

In step S1504, the display unit 231 changes the display position of the CPR image showing another path in accordance with the display position changed in step S1502. More specifically, the amount and direction of movement between the display position before the change and the display position after the change are identified, and the display position of the CPR image showing the other path is changed in accordance with the amount and direction of the movement in interlocking manner. In this case, the display position is changed by keeping the heights of identical branch points equal. In other words, a user can check the images easily even though their display positions are changed. FIG. 16 illustrates a case where the display position is moved from the position in the states illustrated in FIG. 14 closer to the terminal part in steps S1502 and S1504. The origin part and the branch point B1 displayed in FIG. 14 are off the display area in FIG. 16, and the branch point B2, the branch point B3, the branch point B4, the branch point B5, and the terminal part D3 are displayed in FIG. 16. From FIG. 16, it is understood that the heights of the branch point B2 and the branch point B3, which are identical branch points, are kept. Keeping the heights of identical branch points equal even when the display positions thereof are moved enables a user to check them easily.

As described above, when paths of a tubular structure including branch points are displayed, a path including an identical branch point to that in another path can be displayed at a proper display magnification. The display magnification or display position of one of the paths may be changed by keeping the state that the identical branch points can be compared easily.

The paths displayed in the CPR image comparison screen extend from the origin part through a selected terminal part but may extend through two points designated by a user. In this case, there is a possibility that the paths being displayed do not include an identical branch point. Therefore, in a case where the paths being displayed include an identical branch point, the operations in step S1303 and step S1304 and step S1503 and step S1504 are executed. On the other hand, in a case where the paths being displayed do not include an identical branch point, the operations in those steps may not be executed. Three or more CPR images showing a path may be displayed.

Next, a second embodiment will be described. The second embodiment is a variation example of the first embodiment. Like numbers refer to like parts throughout in the descriptions of the first and second embodiments, and the repetitive description will be omitted.

Because the hardware configuration of the medical image diagnosis apparatus 100 according to the second embodiment is the same as that of the first embodiment, the repetitive description will be omitted.

Figure 17:
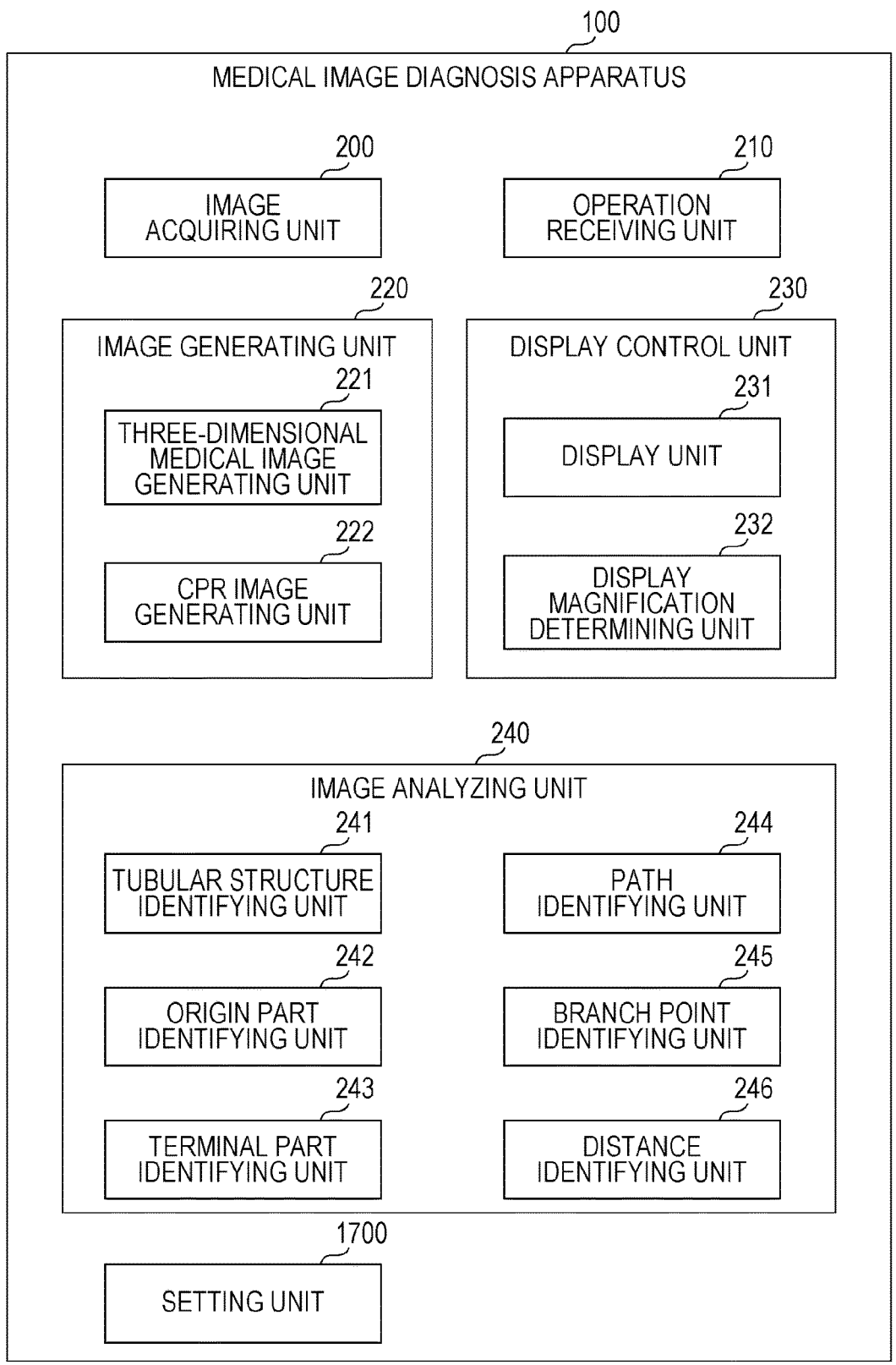
FIG. 17 illustrates an example of a functional configuration of a medical image diagnosis apparatus according to a second embodiment.

FIG. 17 illustrates an example of a functional configuration of the medical image diagnosis apparatus 100 according to the second embodiment. The functions illustrated in FIG. 17 are components implemented by the hardware and programs illustrated in FIG. 1. It should be understood that the functional configuration of the medical image diagnosis apparatus 100 is not limited thereto. The descriptions regarding the same functions as those in FIG. 2 will be omitted.

The medical image diagnosis apparatus 100 further includes a setting unit 1700 in addition to the functional units illustrated in FIG. 2. The setting unit 1700 is a functional unit configured to set operations to be performed in the medical image diagnosis apparatus 100. The setting unit 1700 generates a dialog (or window) for changing a setting, displays it by means of the function of the display unit 231 and stores a setting received in the operation receiving unit 210 in the external memory 111 or RAM 103. A setting stored therein is read out as required, and a corresponding operation to be performed by the medical image diagnosis apparatus 100 is changed.

Next, with reference to FIG. 18 to FIG. 20, a flow of processing for changing a setting will be described.

Figure 18:
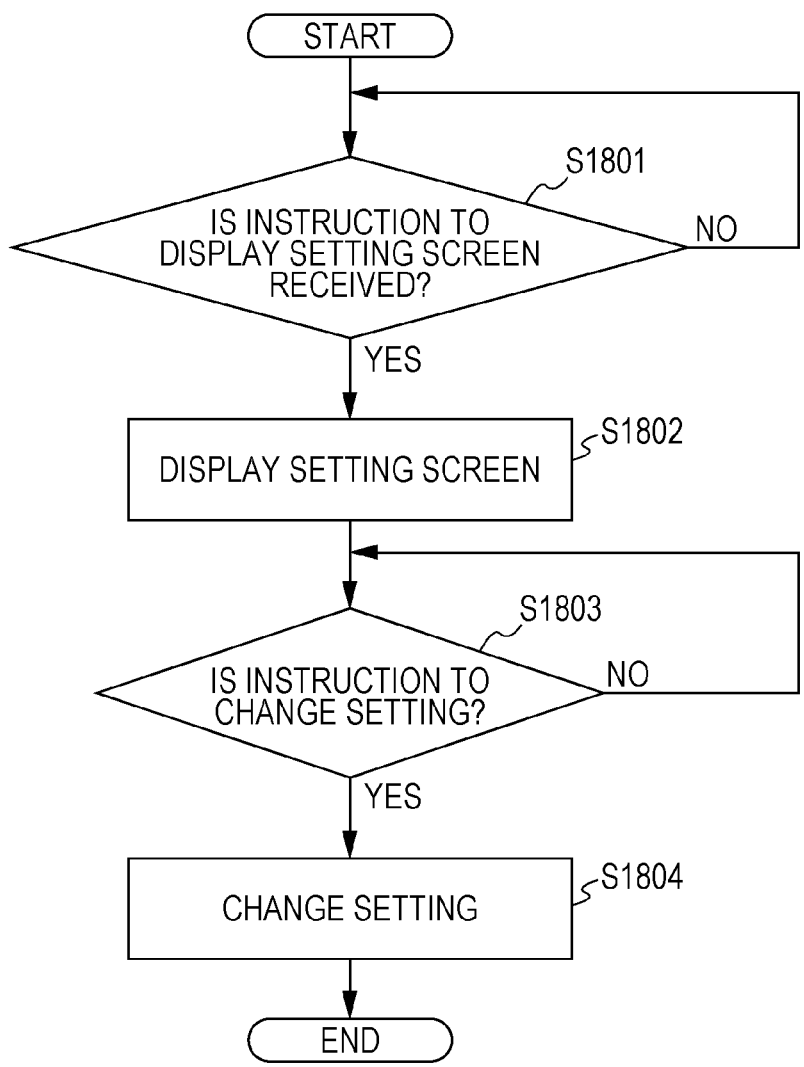
FIG. 18 is a flowchart illustrating an example of processing for displaying a configuration change screen and changing a setting.

FIG. 18 is a flowchart illustrating an example of a flow of processing for displaying a setting change screen and changing a setting. The operations in steps S1801 to S1804 are executed by the CPU 101 in the medical image diagnosis apparatus 100. The details of processing and the order of operations are given in FIG. 18 for illustration purpose only, and an embodiment of the present invention is not limited thereto.

In step S1801, the operation receiving unit 210 determines whether an instruction to change a setting is received or not. If it is determined that an instruction to change a setting is received, the processing proceeds to step S1802. If not, the processing waits without proceeding to step S1802.

Figure 19:
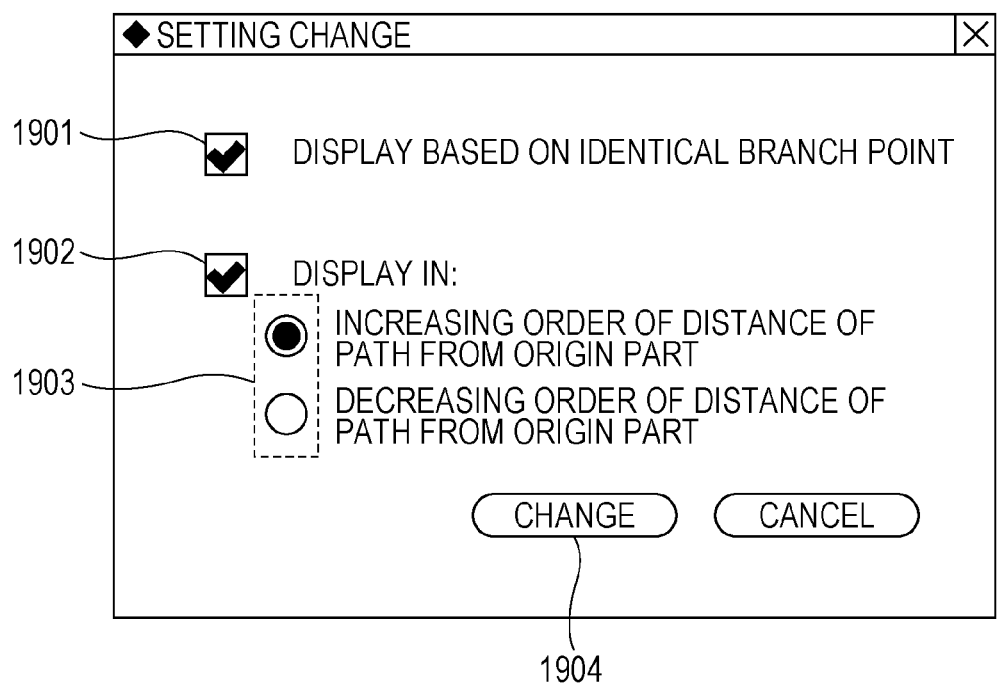
FIG. 19 illustrates an example of a screen configuration of a setting change screen.
Figure 20:
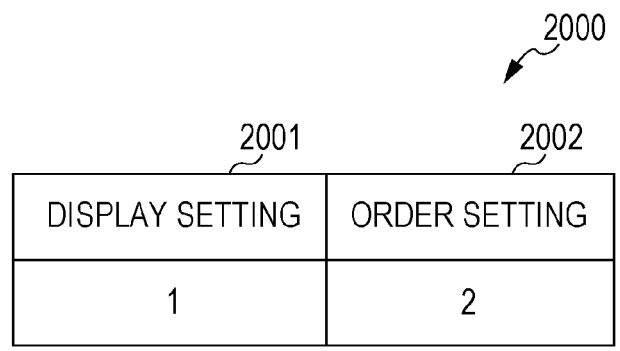
FIG. 20 illustrates an example of a table configuration of setting information table.

In step S1802, the display unit 231 displays on the display 110 a setting change screen as illustrated in FIG. 19, which is generated by the setting unit 1700. The setting change screen includes a display setting check box 1901, an order setting check box 1902, and an order setting radio button 1903. When the display setting check box 1901 is checked and if there is a plurality of CPR images to be displayed, a mode is turned on in which an identical branch point on paths shown in the CPR images are displayed at an equal height. When the order setting check box 1902 is checked and if there is a plurality of CPR images to be displayed, the order of the CPR images can be designated with the order setting radio button 1903. The order setting radio button 1903 may be used to select whether a plurality of CPR images is to be displayed in increasing order of distance of the shown path from an origin part or the plurality of CPR images are to be displayed in decreasing order of distance the shown path from the origin part.

In step S1803, the operation receiving unit 210 determines whether an instruction to change a setting is received through the setting change screen or not. It may be determined whether selections are input through the selection forms on the setting change screen and a change button 1904 included in the setting change screen is then pressed or not. If it is determined that an instruction for the setting change is received, the processing proceeds to step S1804. If not, the processing waits without proceeding to step S1804.

In step S1804, the setting unit 1700 changes a setting instructed and received through the setting change screen. The received setting is stored in a setting information table 2000 as illustrated in FIG. 20. The setting information table 2000 is stored in the external memory 111 or the RAM 103 and includes items of display setting 2001 and order setting 2002. The display setting 2001 is an item under which 1 is stored when the display setting check box 1901 is ON or 0 is stored when it is OFF. The order setting 2002 is an item under which 0 is stored when the order setting check box 1902 is OFF, 1 is stored when displaying in increasing order of distance of the path from the origin part is selected with the order setting radio button 1903, and 2 is stored when displaying in decreasing order is selected.

Next, with reference to FIG. 21 to FIG. 23, a flow of processing for displaying CPR images according to the second embodiment will be described.

Figure 21:
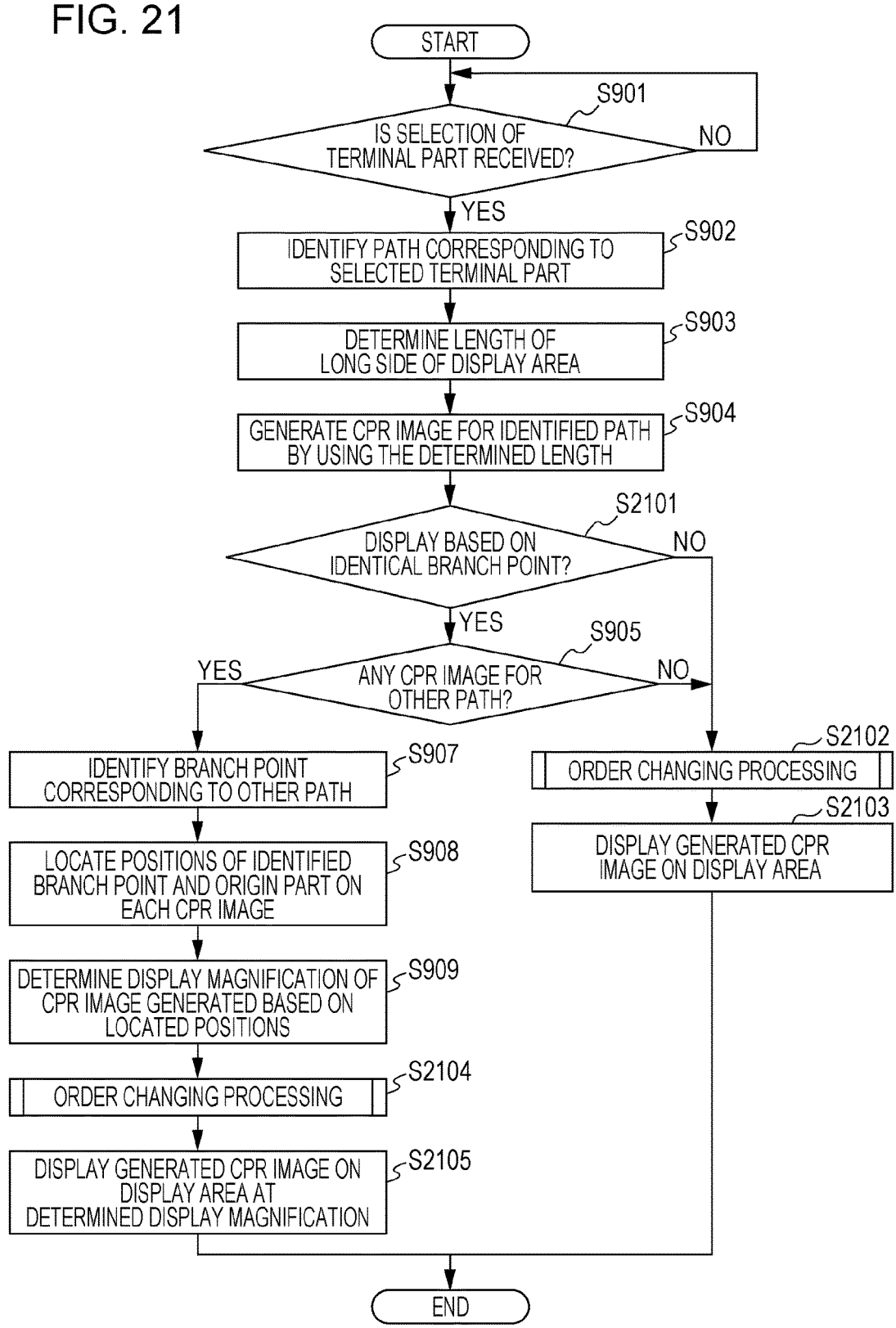
FIG. 21 is a flowchart illustrating an example of a flow of processing for displaying a CPR image showing from an origin part to a selected terminal part of a tubular structure according to the second embodiment.

FIG. 21 is a flowchart illustrating an example of a flow of processing for displaying CPR images from an origin part to a selected terminal part of a tubular structure. The operations in steps S901 to S910 and steps S2101 to S2105 are executed by the CPU 101 in the medical image diagnosis apparatus 100. The details of processing and the order of operations are given in FIG. 21 for illustration purpose only, and an embodiment of the present invention is not limited thereto. Because the operations in steps S901 to S910 are the same as those in FIG. 9, the repetitive description will be omitted.

Upon completion of the processing in step S904, the setting unit 1700 in step S2101 determines whether display setting 2001 is storing 1 or not. In other words, if there is a plurality of CPR images to be displayed, whether a mode is on in which an identical branch point on paths shown in the CPR images are displayed at an equal height. If so, the processing moves to step S905. If not, that is, if it is determined that the display setting 2001 is storing 0, the processing moves to step S2102. In this manner, whether identical branch points are to be displayed at an equal height or not may be switched in accordance with the setting.

If it is not determined in step S905 that there is a CPR image showing another path being displayed or if it not determined in step S2101 that the mode in which CPR images are displayed based on identical branch points is ON, the processing moves to step S2102. In step S2102, processing for determining the order of CPR images based on the order setting 2002 is executed. Details of the order determination processing are illustrated in FIG. 22, which will be described below.

In step S2103, the display unit 231 displays in the CPR image display areas 802 the CPR image generated in step S904 and the CPR image being displayed in the order determined in step S2104. Because there is a plurality of CPR image display areas 802 as described above, the CPR image display areas 802 may be determined so as to display CPR images in increasing order of distance from an origin part from the left side of a screen to the right side of the screen, for example. In accordance with this, the display magnification 742 and terminal part ID 711 in the display area information table 740 are updated. CPR images are displayed in the determined CPR image display areas 802. Furthermore, terminal parts of paths being displayed in the CPR image display areas 802 and correspondences between the paths being displayed and regions of the tubular structure may be displayed in the tubular structure display area 801. For example, the path on the tubular structure corresponding to the terminal part selected in the tubular structure or the terminal part and the CPR image display areas 802 displaying CPR images of the path corresponding to the terminal part are indicated by an identical character string, an identical symbol or an identical color to indicate the correspondence relation. The display superimposed on a tubular structure can be realized by using the path information table 720 and the terminal part information table 710 in FIG. 7. FIG. 23 illustrates an example of a screen displaying character strings such as "PATH 1" and "PATH 2" for a path on a tubular structure corresponding to a terminal part of the tubular structure and CPR image display areas 802 displaying CPR images of the path corresponding to the terminal part. Thus, which path on the tubular structure corresponds to the currently displayed CPR images can be identified. Furthermore, in step S2103, each of the CPR images is displayed without changing its display magnification even though there is another path being displayed. In other words, they are displayed in a conventional display form.

On the other hand, if it is determined in step S905 that there is a CPR image showing another path being displayed and after the display magnification for the generated CPR image is determined, the processing moves to step S2104. In step S2104, processing for determining the order of the CPR images based on the order setting 2002 is performed. Details of the order determination processing are illustrated in FIG. 22, which will be described below.

In step S2105, the display unit 231 displays the CPR image generated in step S904 and a CPR image being displayed in the CPR image display area 802 in the order determined in step S2104. The CPR image generated in step S904 is displayed at the display magnification determined in step S909. Because a plurality of CPR image display areas 802 are provided as described above, the CPR image display areas 802 are determined such that CPR images can be displayed in increasing order of distance from an origin part from the left side of the screen to the right side of the screen, for example. Based on this, the display magnification 742 and the terminal part ID 711 in the display area information table 740 are updated. Then, CPR images are displayed in the determined CPR image display areas 802. FIG. 23 illustrates the result of the change of the order in that way. FIG. 23 illustrates an example of the result of the change of the order illustrated in FIG. 12 to the increasing order of distance from an origin part. A path in a terminal part closer to the origin part is displayed on the left side of the screen while a path in a terminal part farther from the origin part is displayed on the right side of the screen. Thus, a user can compare a plurality of paths easily. It should be noted that CPR images may be displayed in increasing order of distance from the origin part from the right side of the screen to the left side of the screen.

Figure 22:
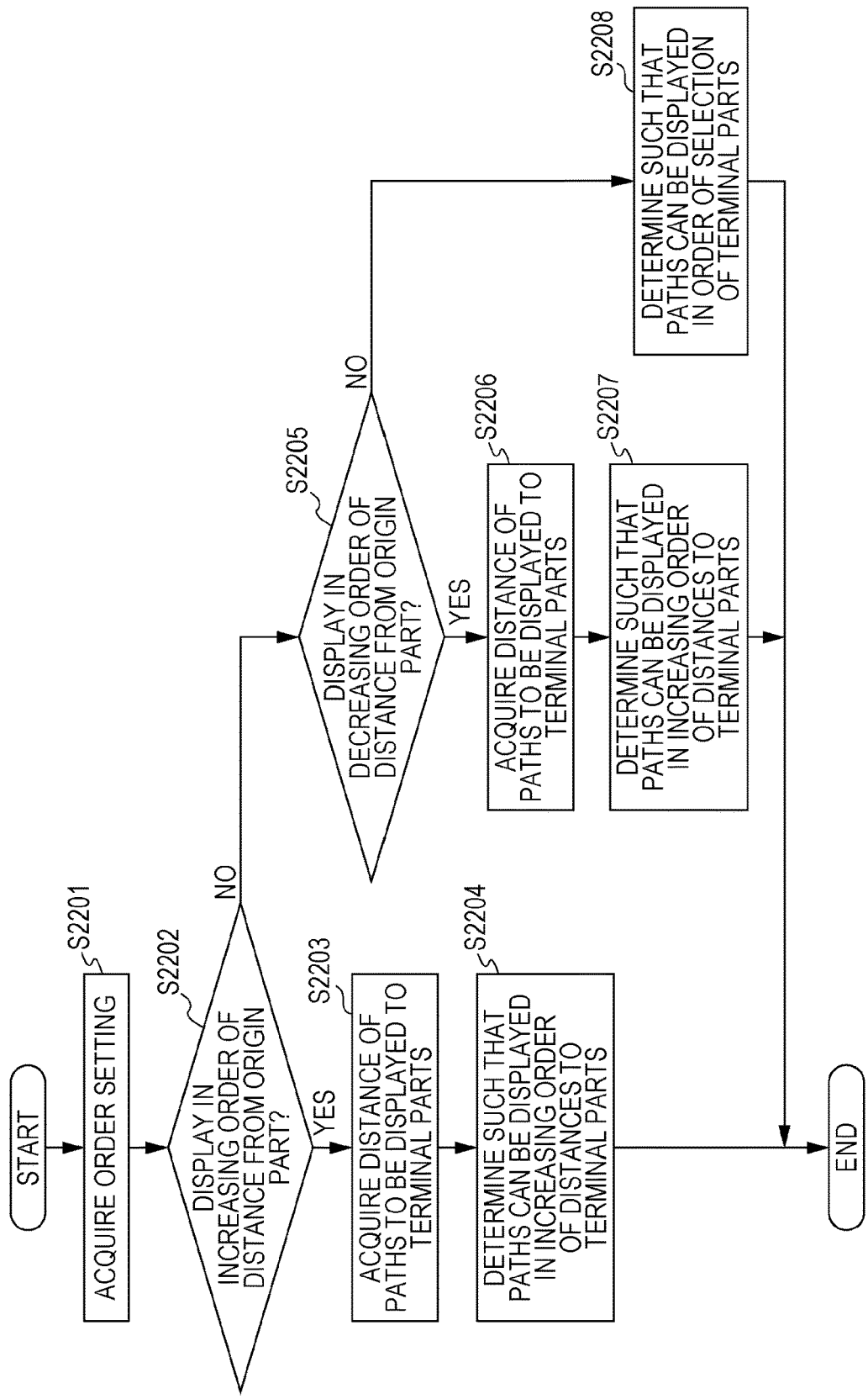
FIG. 22 is a flowchart illustrating an example of a detail flow of processing for order determination processing.
Figure 23:
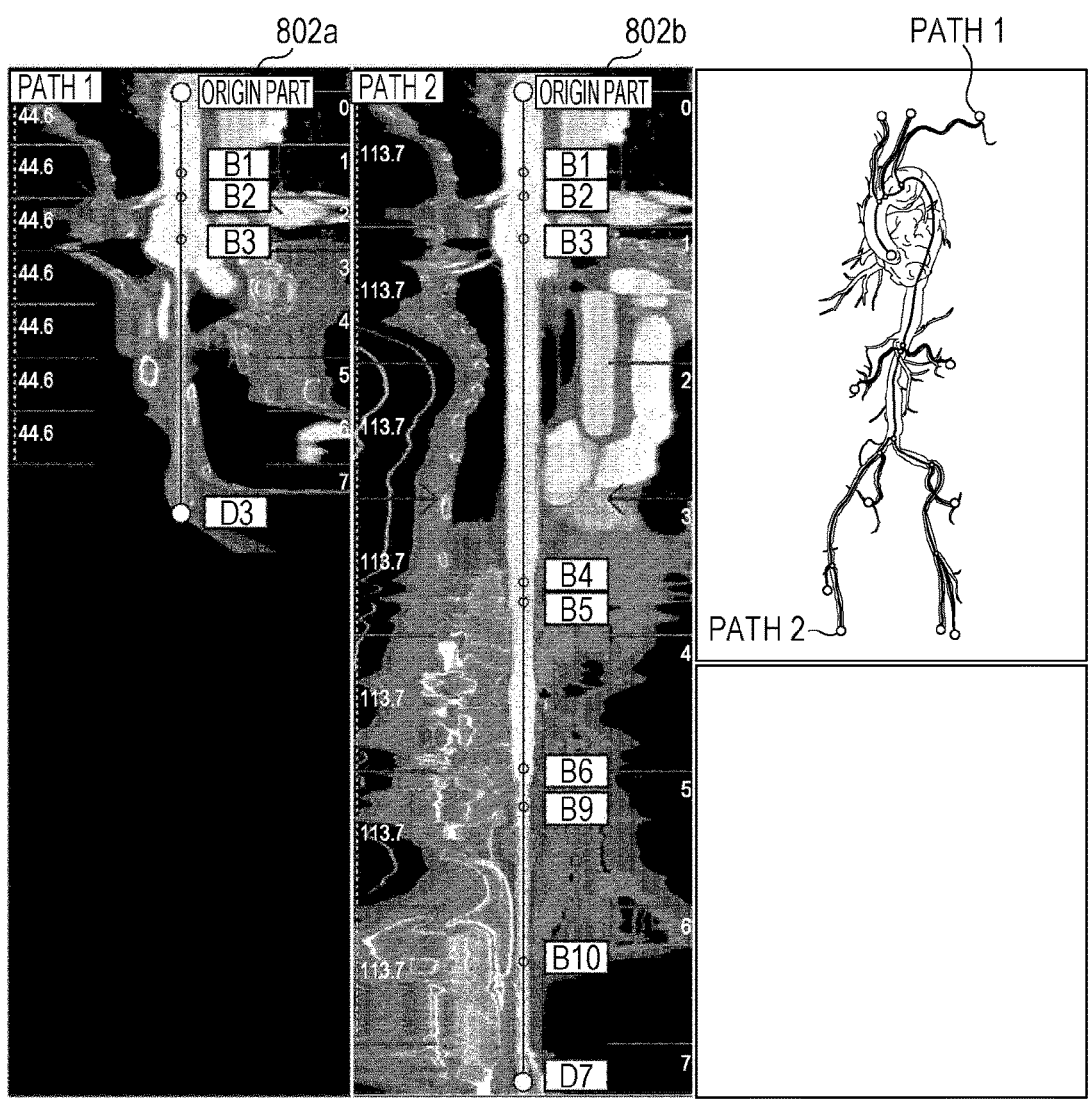
FIG. 23 illustrates an example of CPR images displayed in a determined order.

FIG. 22 is a flowchart illustrating an example of a detail flow of the order determination processing. The operations in steps S2201 to S2208 are executed by the CPU 101 in the medical image diagnosis apparatus 100. The details of processing and the order of operations are given in FIG. 22 for illustration purpose only, and an embodiment of the present invention is not limited thereto. Because the operations in steps S2201 to S2208 are the same as those in FIG. 22, the repetitive description will be omitted.

In step S2201, the setting unit 1700 acquires the order setting 2002 in the setting information table 2000. In step S2202, the setting unit 1700 determines whether the setting in the order setting 2002 acquired in step S2201 is display in increasing order from an origin part or not. If so, the processing moves to step S2203. If not, the processing moves to step S2205.

In step S2203, the distance identifying unit 246 acquires a distance from an origin part to a terminal part of each path shown in each of CPR images displayed in the CPR image display areas 802. The distance corresponding to the path to be displayed is acquired from the terminal part distance 713 in the terminal part information table 710 storing distances from the origin part to terminal parts. The origin part and terminal part of the CPR image to be displayed may be identified to measure the distance.

In step S2204, the display unit 231 compares the distances of the paths acquired in step S2203 and thus determines the order of CPR images in increasing order of distance (or increasing order of distance from the origin part).

In step S2202, the setting unit 1700 determines whether the setting in the order setting 2002 acquired in step S2201 is display in decreasing order from the origin part or not. If so, the processing moves to step S2206. If not, the processing moves to step S2208.

In step S2206, the distance identifying unit 246 acquires the distance from the origin part to the terminal part of each of paths shown in the CPR images displayed in the CPR image display areas 802. The distance corresponding to the path to be displayed is acquired from the terminal part distance 713 in the terminal part information table 710 storing distances from the origin part to terminal parts. The origin part and terminal part of the CPR image to be displayed may be identified to measure the distance.

In step S2207, the display unit 231 compares the distances of the paths acquired in step S2206 and thus determines the order of CPR images in decreasing order of distance (or decreasing order of distance from the origin part).

In step S2208, the display unit 231 determines such that the CPR images are displayed in order of selection of terminal parts. In other words, CPR images are displayed in order of display of the CPR images because a CPR image is generated and is displayed every time a terminal part is selected.

The order of CPR images to be displayed may be determined in the manner as described above and may be used in steps S2103 and S2105 so that the CPR image can be displayed in the order based on the corresponding setting.

As described above, when paths of a tubular structure including branch points are displayed, a path including an identical branch point to that of another path can be displayed at a proper display magnification. Whether a path including an identical branch point to that of another path is to be displayed at a proper display magnification or not may be switched in accordance with the setting.

Aspects of the present invention can be embodied as a system, an apparatus, a method, a program or a storage medium, for example. More specifically, they are applicable to a system including a plurality of apparatuses or an apparatus including one device.

An embodiment of the present invention can be also achieved by supplying a software program which implements a function of the aforementioned embodiment directly or remotely to the system or apparatus. An embodiment that is achieved by reading out and executing the supplied program code by an information processing apparatus in the system or apparatus is also included in aspects of the present invention.

Therefore, aspects of the present invention can also be implemented by program code itself to be installed in the information processing apparatus for implementing function processing of aspects of the present invention in an information processing apparatus. In other words, aspects of the present invention may also include a computer program itself for implementing the function processing of the aspects of the present invention.

In this case, aspects of the present invention may be embodied by object code, a program executed by an interpreter, script data supplied to an OS or the like if it has a function of the program.

The program may be supplied in a recording medium such as a flexible disk, a hard disk, an optical disk, a magneto-optical disk, an MO, a CD-ROM, a CD-R, and a CD-RW.

The recording medium may further be a magnetic tape, a nonvolatile memory card, a ROM, a DVD (DVD-ROM, DVD-R) or the like.

In addition, the program may be supplied from a web site accessible over the Internet through a browser of a client computer. The computer program of aspects of the present invention itself or a compressed file of the computer program including an automatic install function may be downloaded to a recording medium such as a hard disk.

The program code of aspects of the present invention may be divided into a plurality of files so that the files can be downloaded from different web sites. In other words, aspects of the present invention further includes a WWW server from which a plurality of users can download the program file for implementing the function processing of aspects of the present invention in an information processing apparatus.

The program of aspects of the present invention may be encrypted, be stored in a storage medium such as a CD-ROM and be distributed to a user. A user who satisfies a predetermined condition is allowed to download key information for solving the encryption from a web site over the Internet. By using the downloaded key information, the encrypted program may be executed to be installed in an information processing apparatus for implementation.

The functions of the aforementioned embodiments may be realized by an information processing apparatus by reading out and executing the program. In addition, an OS running on an information processing apparatus may implement a part or all of actual processes based on instructions from the program so that the processes can realize the functions of the aforementioned embodiments.

Furthermore, the program read out from a recording medium may be written in a memory provided in a function expanding board inserted to an information processing apparatus or a function expanding unit connected to an information processing apparatus. After that, a CPU provided in the function expanding board or function expanding unit may execute a part or all of actual processes based on instructions from the program so that the processes can realize the functions of the aforementioned embodiments.

It should be understood that the aforementioned embodiments are given only for purpose of illustration of specific examples for embodying aspects of the present invention, and it should not be interpreted that the technical scope of aspects of the present invention is limited thereby. In other words, aspects of the present invention may be embodied in various forms without departing from the technical idea or main features of aspects of the present invention.

While aspects of the present invention have been described with reference to exemplary embodiments, it is to be understood that the aspects of the invention are not limited to the disclosed exemplary embodiments. The scope of the following claims is to be accorded the broadest interpretation so as to encompass all such modifications and equivalent structures and functions.

This application claims the benefit of Japanese Patent Application No. 2015-074604, filed Mar. 31, 2015, which is hereby incorporated by reference herein in its entirety.

What is claimed is:

1. A medical image processing apparatus comprising:
a display control unit configured to cause a display unit to display a first image representing a first path and a second image representing a second path, wherein the first image and the second image are generated separately based on the first path and the second path respectively and displayed separately from each other, wherein the first path and the second path are tubular structures identified from a medical image, wherein the first image and the second image are straightened Curved Multi Planer Reconstruction (CPR) images;
a distance identifying unit configured to identify a distance between two points on a path of the tubular structures, and
a display magnification determining unit configured to determine a display magnification of at least one of the first image and the second image displayed in the display unit based on the identified distance so that a length on the first image from an origin part to a branch point of the first path and a length on the second image from the origin part to a branch point of the second path are equal, wherein the branch point of the first path is identical to the branch point of the second path,
wherein the display control unit causes the display unit to display at least one of the first image and the second image at the display magnification determined by the display magnification determining unit.

2. The medical image processing apparatus according to claim 1, further comprising a selection receiving unit configured to select a terminal part of the tubular structure on a medical image showing the tubular structure,
wherein the first path is a path from an origin part of the tubular structure to a first terminal part selected by the selection receiving unit, and the second path is a path from the origin part to a second terminal part selected by the selection receiving unit, wherein the first terminal part differs from the second terminal part.

3. The medical image processing apparatus according to claim 1, further comprising a cross-sectional image generating unit configured to generate a cross-sectional image showing a path from an origin part of the tubular structure to a plurality of terminal parts of the tubular structure,
wherein the display control unit causes the display unit to display the cross-sectional image showing the first path as the first image and the cross-sectional image showing the second path as the second image at the display magnification determined by the display magnification determining unit.

4. The medical image processing apparatus according to claim 3, wherein the cross-sectional image generating unit identifies a core line showing a path from the origin part of the tubular structure to the plurality of terminal parts of the tubular structure and generates a cross-sectional image based on a cross-section passing through the core line.

5. The medical image processing apparatus according to claim 1, wherein the display control unit causes the display unit to display the first image and the second image in an order determined based on a distance of the first path from an origin part of the tubular structure and a distance of the second path from the origin part of the tubular structure.

6. The medical image processing apparatus according to claim 1, wherein the first path is one of a plurality of paths from an origin part of the tubular structure to a plurality of terminal parts and the second path is another of the plurality of paths.

7. The medical image processing apparatus according to claim 1, wherein the display control unit:
causes the display unit to display the first image at a first display magnification in a case where the first image is displayed; and
causes the display unit to display the first image at a second display magnification lower than the first display magnification in a case where a second path having a longer path length than that of the first path and having a partial path common to the first path and the second image is displayed along with the first image.

8. A medical image processing apparatus comprising:
a display control unit configured to cause the display unit to display, separately, a first image and a second image each representing paths including an origin part and mutually different terminal parts, the origin part and the terminal parts being portions of a tubular structure, wherein the plurality of terminal parts branch from the origin part at a plurality of branch points identified from a medical image, wherein the first image and the second image are straightened Curved Multi Planer Reconstruction (CPR) images;
a distance identifying unit configured to identify a distance between two points on a path of e tubular structures; and
a display magnification determining unit configured to determine a display magnification for the second image representing a second path of the paths having an identical branch point to that of a first path of the paths in the first image displayed by the display unit based on the identified distance and in accordance with each of positions where the plurality of branch points of the first path is displayed so that a length on the first image from an origin part to a branch point of the first path and a length on the second image from the origin part to a branch point of the second path are equal, wherein the branch point of the first path is identical to the branch point of the second path,
wherein the display control unit causes the display unit to display the second image at the display magnification determined by the display magnification determining unit.

9. The medical image processing apparatus according to claim 8, further comprising:
a selection receiving unit configured to select a terminal part of the tubular structure on a medical image showing the tubular structure,
wherein the first path is a path from the origin part of the tubular structure to a first terminal part being selected by the selection received by the selection receiving unit for the terminal part and the second path is a path from the origin part to a second terminal part being selected by the selection received by the selection receiving unit for the terminal part, wherein the first terminal part differs from the second terminal part.

10. The medical image processing apparatus according to claim 8, further comprising a cross-sectional image generating unit configured to generate a cross-sectional image showing a path from the origin part of the tubular structure to a plurality of terminal parts of the tubular structure,
wherein the display control unit causes the display unit to display the cross-sectional image showing the first path as the first image and the cross-sectional image showing the second path as the second image at the display magnification determined by the display magnification determining unit.

11. The medical image processing apparatus according to claim 10, wherein the cross-sectional image generating unit identifies a core line showing a path from the origin part of the tubular structure to the plurality of terminal parts of the tubular structure and generates a cross-sectional image based on a cross-section passing through the core line.

12. The medical image processing apparatus according to claim 8, wherein the display control unit causes the display unit to display the first image and the second image in an order determined based on a distance of the first path from the origin part of the tubular structure and a distance of the second path from the origin part of the tubular structure.

13. The medical image processing apparatus according to claim 8, wherein the first path is one of a plurality of paths from the origin part of the tubular structure to a plurality of terminal parts, and the second path is another of the plurality of paths.

14. The medical image processing apparatus according to claim 8, wherein the display control unit:
   causes the display unit to display the first image at a first display magnification in a case where the first image is displayed; and
   causes the display unit to display the first image at a second display magnification lower than the first display magnification in a case where a second path having a longer path length than that of the first path and having a partial path common to the first path and the second image is displayed along with the first image.

15. A display control method comprising:
   causing a display unit to display a first image representing a first path and a second image representing a second path, wherein the first image and the second image are generated separated based on the first path and the second path, respectively, and are displayed separately from each other, wherein the first path and the second path are tubular structures identified from a medical image, wherein the first image and the second image are straightened Curved Multi Planer Reconstruction (CPR) images;
   identifying a distance between two points on a path of the tubular structures; and
   determining a display magnification of the at least one of the displayed first image and the displayed second image based on the identified distance so that a length on the first image from an origin part to a branch point of the first path and a length on the second image from the origin part to a branch point of the second path are equal, wherein the branch point of the first path is identical to the branch point of the second path,
   wherein the at least one of the first image and the second image are displayed at the determined display magnification.

16. A non-transitory recording medium storing a program for causing a computer to execute a method, the method comprising:
   causing a display unit to display a first image representing a first path and a second image representing a second path, wherein the first image and the second image are generated separated based on the first path and the second path, respectively, and are displayed separately from each other, wherein the first path and the second path are tubular structures identified from a medical image, wherein the first image and the second image are straightened Curved Multi Planer Reconstruction (CPR) images;
   identifying a distance between two points on a path of the tubular structures; and
   determining a display magnification of the at least one of the displayed first image path and the displayed second image based on the identified distance so that a length on the first image from an origin part to a branch point of the first path and a length on the second image from the origin part to a branch point of the second path are equal, wherein the branch point of the first path is identical to the branch point of the second path,
   wherein the at least one of the first image and the second image are displayed at the determined display magnification.

17. A display control method comprising:
   causing a display unit to display, separately, a first image and a second image each representing paths including an origin part and mutually different terminal parts, the origin parts and the terminal parts being portions of a tubular structure, wherein the plurality of terminal parts branch from the origin part at a plurality of branch points identified from a medical image, wherein the first image and the second image arc straightened Curved Multi Planer Reconstruction (CPR) images;
   identifying a distance between two points on a path of the tubular structures; and
   determining a display magnification for the second image representing a second path of the paths having an identical branch point to that of a first path of the paths in the first image displayed based on the identified distance and in accordance with each of positions where a plurality of branch points of the first path is displayed so that a length on the first image from an origin point to a branch point of the first path and a length on the second image from the origin part to a branch point of the second path are equal, wherein the branch point of the first path is identical to the branch point of the second path,
   wherein the second image is displayed at the determined display magnification.

18. A non-transitory recording medium storing a program for causing a computer to execute a method, the method comprising:
   causing a display unit to display, separately, a first image and a second image each representing paths including an origin part and mutually different terminal parts, the origin parts and the terminal parts being portions of a tubular structure, wherein the plurality of terminal parts branch from the origin part at a plurality of branch points identified from a medical image, wherein the first image and the second image are straightened Curved Multi Planer Reconstruction (CPR) images;
   identifying a distance between two points on a path of the tubular structures; and
   determining a display magnification for the second image representing a second path of the paths having an identical branch point to that of a first path of the paths in the first image displayed based on the identified distance in accordance with each of positions where a plurality of branch points of the first path is displayed so that a length on the first image from an origin point to a branch point of the first path and a length on the second image from the origin part to a branch point of the second path are equal, wherein the branch point of the first path is identical to the branch point of the second path,
   wherein the second image is displayed at the determined display magnification.

19. The medical image processing apparatus according to claim 10,
   wherein the cross-section image generating unit generates a straightened CPR image by projecting a cross-sectional curved surface that is a curved surface including a core line indicating a path and is taken from the tubular structure along a longitudinal direction.

20. A medical image processing apparatus comprising:
   a memory storing instructions; and at least one processor that, upon execution of the instructions is configured to cause a display unit to display a first image representing a first path and a second image representing a second path, wherein the first image and the second image are generated separately based on the first path and the second path respectively and displayed separately from each other, wherein the first path and the second path are tubular structures identified from a medical image, wherein the first image and the second image are straightened Curved Multi Planer Reconstruction (CPR) images;

identify a distance between two points on a path of the tubular structures; and determine a display magnification of at least one of the first image and the second image displayed in the apparatus based on the identified distance so that a length on the first image from an origin part to a branch point of the first path and a length on the second image from the origin part to a branch point of the second path are equal, wherein the branch point of the first path is identical to the branch point of the second path, wherein the apparatus displays at least one of the first image and the second image at the determined display magnification.

21. The medical image display apparatus according to claim 4, further comprising a branch-point identifying unit configured to identify a branch point of the tubular structures;

wherein the branch-point identifying unit identifies a part where the core line of the tubular structure diverges as the branch point.

22. A medical image processing apparatus comprising:
a path identifying unit configured to identify a first path of a tubular structure identified based on a medical image and a second path of the tubular structure;
an image generating unit configured to generate a first image representing the first path and a second image representing the second path, wherein the first image and the second image are straightened Curved Multi Planer Reconstruction (CPR) images;
a distance identifying unit configured to identify a distance between two points on a path of the tubular structure;
a display magnification determining unit configured to determine a display magnification of at least one of the first image and the second image using the identified distance so that a branch point of the first path on the first image and a branch point of the second path on the second image are displayed at positions adjacent to each other, wherein the branch point of the second path is identical to the branch point of the first path; and
a display control unit configured to cause a display unit to display the first image and the second image,
wherein the display control unit causes the display unit to display at least one of the first image and the second image at the determined display magnification.

23. The medical image processing apparatus according to claim 22, wherein the display control unit causes the display unit to display the first image and the second image side by side.

24. The medical image processing apparatus according to claim 22, wherein the display control unit causes the display unit to display a third image representing the tubular structure generated by performing volume rendering.

25. The medical image processing apparatus according to claim 22, wherein the display control unit causes the display unit to display, on the first image and the second image, information representing the branch point.

26. The medical image processing apparatus according to claim 22, wherein, in a case where an instruction is received from a user, the display control unit causes the display unit to display at least one of the first image and the second image at the determined display magnification.

27. The medical image processing apparatus according to claim 22, wherein the first path includes a origin part and a first terminal part of the tubular structure, and the second path includes the origin part and a second terminal part of the tubular structure.

28. The medical image processing apparatus according to claim 22, wherein the tubular structure is a blood vessel.

29. The medical image processing apparatus according to claim 22, wherein the first path and the second path are core lines of the tubular structure.

30. A medical image processing method comprising:
identifying a first path of a tubular structure identified based on a medical image and a second path of the tubular structure;
generating a first image representing the first path and a second image representing the second path, wherein the first image and the second image are straightened Curved Multi Planer Reconstruction (CPR) images;
identifying a distance between two points on a path of the tubular structure;
determining a display magnification of at least one of the first image and the second image using the identified distance so that a branch point of the first path on the first image and a branch point of the second path on the second image are displayed at positions adjacent to each other, wherein the branch point of the second path is identical to the branch point of the first path; and
causing a display unit to display the first image and the second image,
wherein the causing includes causing the display unit to display at least one of the first image and the second image at the determined display magnification.

31. The medical image processing method according to claim 30, wherein the causing includes causing the display unit to display the first image and the second image side by side.

32. The medical image processing method according to claim 30, wherein the causing includes causing the display unit to display a third image representing the tubular structure generated by performing volume rendering.

33. The medical image processing method according to claim 30, wherein the causing includes causing the display unit to display, on the first image and the second image, information representing the branch point.

34. The medical image processing method according to claim 30, wherein, in a case where receiving an instruction from a user, the causing includes causing the display unit to display at least one of the first image and the second image at the determined display magnification.

35. The medical image processing method according to claim 30, wherein the first path includes a origin part and a first terminal part of the tubular structure, and the second path includes the origin part and a second terminal part.

36. The medical image processing method according to claim 30, wherein the tubular structure is a blood vessel.

37. The medical image processing method according to claim 30, wherein the first path and the second path are core lines of the tubular structure.

38. A non-transitory recording medium storing a program for causing a computer to execute a method, the method comprising:

identifying a first path of a tubular structure identified based on a medical image and a second path of the tubular structure;

generating a first image representing the first path and a second image representing the second path, wherein the first image and the second image are straightened Curved Multi Planer Reconstruction (CPR) images;

identifying a distance between two points on a path of the tubular structure;

determining a display magnification of at least one of the first image and the second image using the identified distance so that a branch point of the first path on the first image and a branch point of the second path on the second image are displayed at positions adjacent to each other, wherein the branch point of the second path is identical to the branch point of the first path; and causing a display unit to display the first image and the second image, wherein the causing includes causing the display unit to display at least one of the first image and the second image at the determined display magnification.

* * * * *